US012751740B2

(12) United States Patent
Drain et al.

(10) Patent No.: US 12,751,740 B2
(45) Date of Patent: Oct. 6, 2026

(54) SURGICAL INSTRUMENT WITH ORIENTATION SENSOR HAVING DIFFERENT MODES AND A USER IDENTIFIED HEADING

(71) Applicant: Prichard Medical, Inc., Rocky River, OH (US)

(72) Inventors: Joseph Prichard Drain, Columbus, OH (US); Keith Alsberg, Evanston, IL (US); Jeremiah Peter O'Leary, Chicago, IL (US)

(73) Assignee: Prichard Medical, Inc., Rocky River, OH (US)

( * ) Notice: Subject to any disclaimer, the term of this patent is extended or adjusted under 35 U.S.C. 154(b) by 972 days.

(21) Appl. No.: 17/701,266

(22) Filed: Mar. 22, 2022

(65) Prior Publication Data

US 2022/0211416 A1 Jul. 7, 2022

Related U.S. Application Data

(63) Continuation-in-part of application No. PCT/US2021/022964, filed on Mar. 18, 2021, which (Continued)

(51) Int. Cl.

| | |
|---|---|
| ***A61B 17/66*** | (2006.01) |
| ***G16H 40/63*** | (2018.01) |
| *A61B 17/00* | (2006.01) |

(52) U.S. Cl.

CPC ............. *A61B 17/66* (2013.01); *G16H 40/63* (2018.01); *A61B 2017/00199* (2013.01); *A61B 2017/00455* (2013.01); *A61B 2560/0487* (2013.01)

(58) Field of Classification Search

CPC ........... A61B 17/66; A61B 2017/00455; A61F 2/4609

See application file for complete search history.

(56) References Cited

U.S. PATENT DOCUMENTS 5,832,422 A 11/1998 Wiedenhoefer
5,953,683 A 9/1999 Hansen et al.

(Continued)

FOREIGN PATENT DOCUMENTS

AU 2013204920 B2 6/2015
EP 1635705 B1 1/2012

(Continued)

OTHER PUBLICATIONS

Bosch Sensortec; BNO055 Intelligent 9-axis absolute orientation sensor; Data Sheet; Document Revision 1.4; Date Jun. 2016; Doc. No. BST-BNO055-DS00-14; 106 pages.

(Continued)

*Primary Examiner* — Erin Mcgrath
(74) *Attorney, Agent, or Firm* — BakerHostetler

(57) ABSTRACT

An orientation sensor that includes a user input device that is configured to transition a mode of the orientation sensor and/or that includes a movable guide member. The user input device may include a button, and in response to pressing the button the mode of the orientation sensor may change (e.g., to provide inclination values of an impactor shaft when the patient is in a different position). The orientation sensor may include a display that is configured to display at least one first orientation value in a first mode and at least one second orientation value in a second mode. The orientation sensor may include an actuation member configured to actuate the movable guide member, for example, from a first position where an impactor shaft may be (Continued)

received in the guide to a second position where the guide may attach to the impactor shaft.

37 Claims, 23 Drawing Sheets

Related U.S. Application Data is a continuation of application No. 17/121,006, filed on Dec. 14, 2020, now Pat. No. 10,952,775.

(56) References Cited

U.S. PATENT DOCUMENTS

| | | | | |
|---|---|---|---|---|
| 7,559,931 | B2 | 7/2009 | Stone | |
| 8,057,482 | B2 | 11/2011 | Stone et al. | |
| 8,118,815 | B2 | 2/2012 | Van Der Walt | |
| 8,241,296 | B2 | 8/2012 | Wasielewski | |
| 8,740,810 | B2 | 6/2014 | Sanbuichi | |
| 8,814,877 | B2 | 8/2014 | Wasielewski | |
| 8,888,786 | B2 | 11/2014 | Stone et al. | |
| 9,532,730 | B2 | 1/2017 | Wasielewski | |
| 9,795,451 | B2 | 10/2017 | Gorek et al. | |
| 2009/0318836 | A1 | 12/2009 | Stone et al. | |
| 2010/0064216 | A1* | 3/2010 | Borja | A61B 34/25 715/705 |
| 2010/0076505 | A1 | 3/2010 | Borja | |
| 2010/0125172 | A1 | 5/2010 | Jayaray | |
| 2010/0137869 | A1 | 6/2010 | Borja et al. | |
| 2011/0208093 | A1 | 8/2011 | Gross et al. | |
| 2011/0313281 | A1 | 12/2011 | Grinberg et al. | |
| 2012/0319859 | A1 | 12/2012 | Taub et al. | |
| 2013/0217998 | A1* | 8/2013 | Mahfouz | A61B 8/0875 600/595 |
| 2013/0303845 | A1 | 11/2013 | Skula et al. | |
| 2014/0030669 | A1 | 1/2014 | Hey et al. | |
| 2014/0052149 | A1 | 2/2014 | Van Der Walt et al. | |
| 2015/0119637 | A1 | 4/2015 | Alvarez et al. | |
| 2015/0127009 | A1 | 5/2015 | Berend et al. | |
| 2015/0223890 | A1 | 8/2015 | Miller et al. | |
| 2015/0238204 | A1 | 8/2015 | Stone | |
| 2015/0272696 | A1 | 10/2015 | Fry et al. | |
| 2015/0305786 | A1 | 10/2015 | Wehrle et al. | |
| 2015/0366714 | A1 | 12/2015 | Kandavel et al. | |
| 2016/0242934 | A1 | 8/2016 | Van Der Walt et al. | |
| 2016/0310077 | A1 | 10/2016 | Hunter et al. | |
| 2016/0354162 | A1 | 12/2016 | Yen et al. | |
| 2017/0172458 | A1 | 6/2017 | Kato et al. | |
| 2017/0231709 | A1* | 8/2017 | Gupta | A61B 5/062 600/424 |
| 2018/0055571 | A1 | 3/2018 | Gorek et al. | |
| 2018/0058536 | A1 | 3/2018 | Pathak et al. | |
| 2018/0110569 | A1 | 4/2018 | Drain | |
| 2018/0193171 | A1 | 7/2018 | Van der Walt et al. | |
| 2020/0237446 | A1 | 7/2020 | Drain | |
| 2020/0268454 | A1* | 8/2020 | Walter | A61B 34/20 |
| 2021/0369472 | A1* | 12/2021 | McCarthy | A61F 2/4657 |

FOREIGN PATENT DOCUMENTS

| | | | |
|---|---|---|---|
| GB | 2573014 | A | 10/2019 |
| JP | 2019-534136 | A | 11/2019 |
| WO | WO 2009/055034 | A1 | 4/2009 |
| WO | WO 2013/169674 | A1 | 11/2013 |
| WO | WO 2018/085900 | A1 | 5/2018 |

OTHER PUBLICATIONS

International Patent Application No. PCT/US2020/029882; Int' Written Opinion and Search Report; dated Aug. 3, 2020; 12 pages.

International Patent Application No. PCT/US2021/022964; Int'l Written Opinion and Search Report; dated Jul. 22, 2021; 19 pages.

DASH®Smart Instrument Technologies; Version 1.1; Brainlab AG Germany; © 2014; 490 pages; along with machine translation.

Oraco Galeazzi; "La protesi totale di ginocchio con sistema Dash Brainlab—Dr. M. Ulivi"; https://www.youtube.com/watch?v=xUL8wxyhD8k&rco=1; YouTube; Jun. 2014; accessed Feb. 2026; (timestamps: 1:11-1:19 and 2:25 and 3:41); 5 pages.

European Patent Application No. 21907344.2; Extended Search Report; dated Feb. 18, 2025; 17 pages.

"Winkelmesser, Wasserwaage für 1,2 INV. Android und iOS"; https://www.youtube.com/watch?v=c5dy-jWjFWw; YouTube; Feb. 2019; accessed Sep. 2025; 2 pages; along with machine translation entitled "Protractor, spirit level for Android and iOS".

"iLevel—Protractor & Level"; https://www.youtube.com/watch?v=BXohXhJgetc; YouTube; May 10, 2018; accessed Feb. 18, 2026; 6 pages.

* cited by examiner

SURGICAL INSTRUMENT WITH ORIENTATION SENSOR HAVING DIFFERENT MODES AND A USER IDENTIFIED HEADING

RELATED APPLICATIONS

This application is a continuation-in-part of International Application No. PCT/US2021/022964, filed on Mar. 18, 2021, which is a continuation of U.S. Non-Provisional application Ser. No. 17/121,006 filed on Dec. 14, 2020, granted as U.S. Pat. No. 10,952,277 on Mar. 23, 2021, the contents of each of which are incorporated herein by reference in their entirety.

FIELD OF INVENTION

The disclosure relates generally to instruments, such as medical (e.g., surgical) instruments. For example, this disclosure relates to surgical and other medical instruments including absolute orientation sensors. The instruments of the present disclosure may be used in any suitable procedure or treatment which would benefit from knowing the orientation of such instrument in three-dimensional space. While reference is made herein to surgical instruments in particular, it should be understood that this disclosure is directed to medical, dental, or other instruments used in the treatment of humans or animals requiring orientation knowledge.

BACKGROUND

Some medical procedures rely upon a medical practitioner aligning tools by eye or with a cumbersome alignment guide. For example, when performing a hip replacement surgery a surgeon may use an impactor shaft to install an acetabular cup. The surgeon may use an anteversion guide or an alignment extension to orient the impactor shaft at a 20-degree (20°) anteversion angle relative to a longitudinal body axis of a patient. Also, the surgeon may use an alignment extension to orient an impactor shaft at a 45-degree (45°) inclination/abduction angle relative to the longitudinal body axis of the patient (and relative to a horizontal plane when the patient is lying on their side).

When alignment of the impactor shaft is not proper, misalignment of the acetabular cup occurs, which can cause complications after surgery to arise. Additional surgery may be required to correct the misalignment resulting from the original installation of the acetabular cup.

SUMMARY

The present application provides an orientation sensor that includes a user input device that is configured to change a mode of the orientation sensor and/or includes a movable guide member. The user input device may include a button, and in response to pressing the button the mode of the orientation sensor may change (e.g., to provide inclination values of an impactor shaft when the patient is in a different position). The orientation sensor may include a display that is configured to display at least one first orientation value in a first mode and at least one second orientation value in a second mode. The orientation sensor may include an actuation member configured to actuate the movable guide member, for example, from a first position where an impactor shaft may be received in the guide to a second position where the guide may attach to the impactor shaft.

The orientation sensor may include a memory that is configured to store the heading. The orientation sensor may include a display that is configured to display the at least one orientation value. The orientation sensor may include a processor that is configured to generate orientation information based on the heading. The user input device may include a button, and in response to pressing the button the heading may be set based on the current orientation of the orientation sensor. For example, the at least one orientation value may be associated with orientation data detected by an orientation sensing component, and the at least one orientation value may be displayed based on the heading.

The display may provide the surgeon with real-time feedback of angles that are pertinent to a given surgery. For example, the surgeon may align an axis (e.g., the longitudinal axis) of the orientation sensor with an axis (e.g., a longitudinal body axis) of the patient and provide a predetermined input to the user input device (e.g., press a button of the user input device) to set a heading for the orientation sensor. When the heading is set, the display may display in real-time an angle of an instrument axis (e.g., a central axis of a guide) of the orientation sensor relative to the longitudinal body axis of the patient. For example, the anteversion angle and vertical inclination angle of the central axis of the guide may be displayed in real-time relative to the longitudinal body axis of a patient lying on their side. In an embodiment, the heading may be set to a different axis of the patient and anteversion angle and the vertical inclination angle of the central axis may be displayed in real-time relative to the different axis.

The orientation sensor may be configured to mount to an instrument body. For example, the orientation sensor may include a guide that is configured to receive a shaft of an instrument body as disclosed in U.S. patent application Ser. No. 16/395,986 filed on Apr. 26, 2019 and U.S. patent application Ser. No. 15/619,747 filed on Jun. 12, 2017, both of which both of which are entitled Surgical Instrument With LED Lighting and Absolute Orientation and are hereby incorporated by reference in their entirety. In an embodiment, the surgical instrument includes a housing or other outer structure to which the orientation sensor is configured to be attached or affixed.

The following presents a simplified overview of the example embodiments in order to provide a basic understanding of some aspects of the example embodiments. This overview is not an extensive overview of the example embodiments. It is intended to neither identify key or critical elements of the example embodiments nor delineate the scope of the appended claims. Its sole purpose is to present some concepts of the example embodiments in a simplified form as a prelude to the more detailed description that is presented later.

In accordance with embodiments herein, the present disclosure provides medical instruments and devices having orientation sensors (e.g., absolute orientation sensors) with a button that sets the heading of the orientation sensor based on the orientation of the orientation sensor in response to the button being pressed. The instruments of the present disclosure may be used in any suitable procedure or treatment which would benefit from knowing the orientation of the surgical instrument in relation to a heading set by the user (e.g., the surgeon).

While reference is made herein to surgical instruments in particular, it should be understood that this disclosure is applicable to medical, dental, or other instruments used in the treatment of humans or animals requiring orientation.

An absolute orientation sensor may not require calibration against a known point or plane in order to provide orientation related information. For example, an embodiment of an absolute orientation sensor comprises an accelerometer, a gyroscope, and a magnetometer, and may be able to generate an absolute orientation by using the Earth itself as a reference point or plane, by sensing the Earth's magnetic field, and by extension, the Earth's magnetic core, rather than an arbitrarily determined point or plane. In some embodiments, the orientation sensor does not include a magnetometer. For example, the heading of the orientation sensor may be manually set by the user, as opposed to being set to an arbitrary angle upon activation of the orientation sensor or being set to magnetic north.

According to one aspect of the invention, an orientation sensor comprises: an orientation sensing component, wherein the orientation sensing component is configured to detect a plurality of orientation data, wherein the orientation sensor is configured to be mounted to an instrument body such that when the orientation sensor is mounted to the instrument body the orientation sensing component would be at least partially fixed relative to the instrument body such that a change in orientation of the instrument body in at least one direction would be detected by the orientation sensing component; a display, wherein when the orientation sensor is in a first mode the display is configured to display at least one first orientation value, that is associated with the plurality of orientation data, in real-time, and when the orientation sensor is in a second mode the display is configured to display, in real-time, a respective at least one second orientation value that is associated with the plurality of orientation data and is different from the respective at least one second orientation value; and a user input device, wherein the user input device is configured to transition the display from the first mode to the second mode, in response to the user input device receiving a first predetermined user input.

According to another aspect of the invention, an orientation sensor comprises: a processor; an orientation sensing component operably coupled to the processor, wherein the orientation sensing component is configured to detect a plurality of orientation data, wherein the orientation sensor is configured to be mounted to an instrument body such that when the orientation sensor is mounted to the instrument body the orientation sensing component would be at least partially fixed relative to the instrument body such that a change in orientation of the instrument body in at least one direction would be detected by the orientation sensing component; and a movable guide member that at least partially defines a guide when in a first position, wherein the movable guide member is configured to attach to the instrument body when in the first position, and wherein the movable guide member is configured to open to a second position where the guide is configured to receive the instrument body.

According to another aspect of the invention, an orientation sensor comprising: an orientation sensing component, wherein the orientation sensing component is configured to detect a plurality of orientation data, wherein the orientation sensor is configured to be mounted to an instrument body such that when the orientation sensor is mounted to the instrument body the orientation sensing component would be at least partially fixed relative to the instrument body such that a change in orientation of the instrument body in at least one direction would be detected by the orientation sensing component; a display that is configured to display at least one first orientation value, that is associated with the plurality of orientation data, in real-time; wherein the plurality of orientation data includes rotation data relative to an X-axis, a Y-axis, and a Z-axis, the Y-axis being perpendicular to the X-axis, and the Z-axis being perpendicular to the X-axis and the Y-axis; wherein the orientation sensor includes a guide configured to mount to a shaft of the instrument body, wherein the guide defines a guide axis; and wherein the at least one first orientation value includes an angle of inclination of the guide axis relative to an X-Y plane and/or relative to an X-Z plane, and wherein the at least one first orientation value does not change when the orientation device is rotated about the guide axis.

According to another aspect of the invention, an orientation sensor comprises: a processor; an orientation sensing component operably coupled to the processor, wherein the orientation sensing component is configured to detect a plurality of orientation data, wherein the orientation sensor is configured to be mounted to an instrument body such that when the orientation sensor is mounted to the instrument body the orientation sensing component would be at least partially fixed relative to the instrument body such that a change in orientation of the instrument body in at least one direction would be detected by the orientation sensing component; a display operably coupled to the processor, wherein the display is configured to display at least one orientation value, that is associated with the plurality of orientation data, in real-time; a user input device operably coupled to the processor, wherein the processor is configured to, in response to the user input device receiving a predetermined user input, set a heading based on the orientation of the orientation sensor when the predetermined user input is received by the user input device; wherein the heading is associated with the orientation data such that when the orientation sensor would be held in a predetermined reference orientation relative to the heading, the display displays a predetermined orientation value, and whereby movement of the orientation sensing component in the at least one direction from the predetermined reference orientation would be represented on the display as the at least one orientation value being different from the predetermined orientation value.

According to another aspect of the invention, an orientation sensor comprises: a processor; a memory operably coupled to the processor; an orientation sensing component operably coupled to the processor, wherein the orientation sensing component is configured to detect a plurality of orientation data, wherein the orientation sensor is configured to be mounted to an instrument body such that when the orientation sensor is mounted to the instrument body the orientation sensing component would be at least partially fixed relative to the instrument body such that a change in orientation of the instrument body in at least one direction would be detected by the orientation sensing component; a user input device operably coupled to the processor, wherein, in response to the user input device receiving a predetermined user input, the processor is configured to store, in the memory, a heading based on the orientation of the orientation sensor when the predetermined user input is received by the user input device; wherein the processor is configured to generate orientation information based on the heading, that is stored in the memory, and the current orientation of the orientation sensor; and wherein the heading is associated with the orientation data such that when the orientation sensor would be held in a predetermined reference orientation relative to the heading, processor generates predetermined orientation information, and whereby movement of the orientation sensing component in the at least one direction from the predetermined reference orientation would be represented by the processor generating a first orientation information that is different from the predetermined orientation information.

According to another aspect of the invention, an orientation sensor comprises: an orientation sensing component, wherein the orientation sensing component is configured to detect a plurality of orientation data, wherein the orientation sensor is configured to be mounted to an instrument body such that when the orientation sensor is mounted to the instrument body the orientation sensing component would be at least partially fixed relative to the instrument body such that a change in orientation of the instrument body in at least one direction would be detected by the orientation sensing component; a display, wherein the display is configured to display at least one orientation value, that is associated with the plurality of orientation data, in real-time; a user input device, wherein the user input device is configured to set a heading, in response to the user input device receiving a predetermined user input, based on the orientation of the orientation sensor when the predetermined user input is received by the user input device, wherein the at least one orientation value is based on the heading set by the user input device.

According to another aspect of the invention, an orientation sensor comprises: an orientation sensing component, wherein the orientation sensing component is configured to detect a plurality of orientation data, wherein the orientation sensor is configured to be mounted to an instrument body such that when the orientation sensor is mounted to the instrument body the orientation sensing component would be at least partially fixed relative to the instrument body such that a change in orientation of the instrument body in at least one direction would be detected by the orientation sensing component; a display, wherein the display is configured to display at least one orientation value, that is associated with the plurality of orientation data, in real-time; a user input device, wherein the user input device is configured to set a heading, in response to the user input device receiving a predetermined user input, based on the orientation of the orientation sensor when the predetermined user input is received by the user input device, wherein the at least one orientation value is based on the heading set by the user input device.

According to another aspect of the invention, an orientation sensor comprises: a processor; an orientation sensing component operably coupled to the processor, wherein the orientation sensing component is configured to detect a plurality of orientation data, wherein the orientation sensor is configured to be mounted to an instrument body such that when the orientation sensor is mounted to the instrument body the orientation sensing component would be at least partially fixed relative to the instrument body such that a change in orientation of the instrument body in at least one direction would be detected by the orientation sensing component; and a guide that includes a lateral opening to receive a body of a tool.

According to another aspect of the invention, an orientation sensor comprises: a processor; an orientation sensing component operably coupled to the processor, wherein the orientation sensing component is configured to detect a plurality of orientation data, wherein the orientation sensor is configured to be mounted to an instrument body such that when the orientation sensor is mounted to the instrument body the orientation sensing component would be at least partially fixed relative to the instrument body such that a change in orientation of the instrument body in at least one direction would be detected by the orientation sensing component; and a guide that includes a circumferentially extending slot connected to a longitudinally extending notch.

Features of any of the above aspects may be combined with one another. For example, any above aspect may include the user input device, display, processor, memory, and/or guide of another aspect.

In addition or alternatively, any above aspect may be a part of a surgical instrument. For example, any orientation sensor may be removable from an instrument body of a surgical instrument.

The surgical instrument may comprise a display operatively coupled to the device processor, wherein the display may be operable to display at least a portion of the plurality of generated orientation status data thereon. The plurality of orientation data may comprise at least one from the group consisting of a location data, pitch data, roll data, and yaw data. The location data may comprise x, y, and z coordinate values. The plurality of orientation data may further comprise at least one selected from the group consisting of angular velocity data, acceleration data, magnetic field strength data, linear acceleration data, and gravity data.

The surgical instrument may be one or more: drills, drivers, saws, wire insertion devices, impactors, device inserters, burr, awls, scalpels, suction, retraction devices, mallets, biopsy needles, unpowered drills, unpowered drivers, unpowered saws, unpowered wire inserters, and/or unpowered burrs.

Still other advantages, aspects and features of the subject disclosure will become readily apparent to those skilled in the art from the following description wherein there is shown and described embodiments of the present disclosure, simply by way of illustration of modes suited to carry out the subject disclosure. As it will be realized, the present disclosure is capable of other different embodiments and its several details are capable of modifications in various obvious aspects all without departing from the scope herein. Accordingly, the drawings and descriptions will be regarded as illustrative in nature and not as restrictive.

BRIEF DESCRIPTION OF THE DRAWINGS

The drawings are of illustrative embodiments. They do not illustrate all embodiments. Other embodiments may be used in addition or instead. Details which may be apparent or unnecessary may be omitted to save space or for more effective illustration. Some embodiments may be practiced with additional components or steps and/or without all of the components or steps which are illustrated. When the same numeral appears in different drawings, it refers to the same or like components or steps.

DETAILED DESCRIPTION

Figure 1:
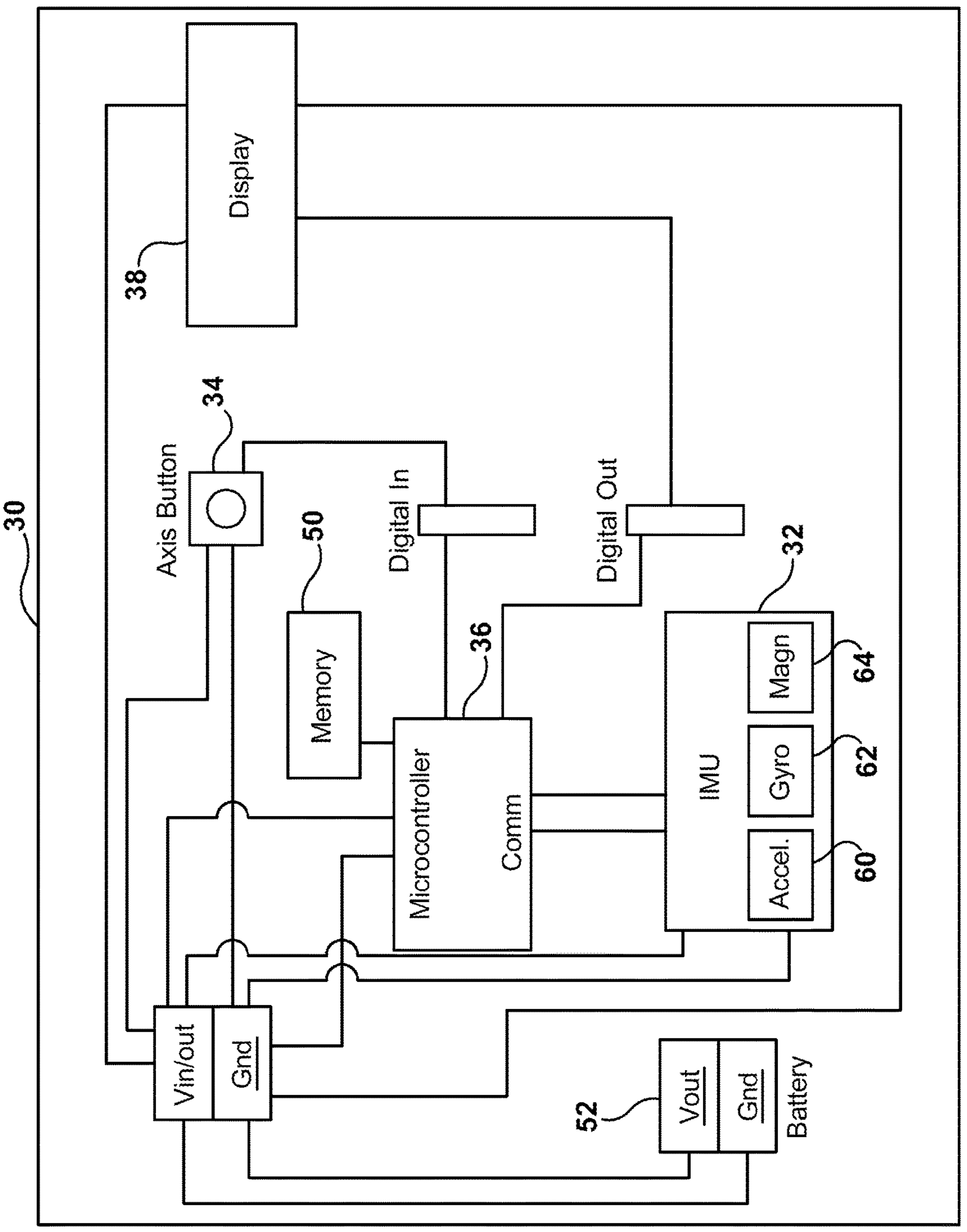
FIG. 1 is a block diagram of an orientation sensor that includes a user input device.

This description provides examples not intended to limit the scope of the appended claims. The figures generally indicate the features of the examples, where it is understood and appreciated that like reference numerals are used to refer to like elements. Reference in the specification to "one embodiment" or "an embodiment" or "an example embodiment" means that a particular feature, structure, or characteristic described is included in at least one embodiment described herein and does not imply that the feature, structure, or characteristic is present in all embodiments described herein.

Before the present methods and systems are disclosed and described, it is to be understood that the methods and systems are not limited to specific methods, specific components, or to particular implementations. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other components, integers or steps. "Exemplary" means "an example of" and is not intended to convey an indication of a preferred or ideal embodiment. "Such as" is not used in a restrictive sense, but for explanatory purposes.

Disclosed are components that may be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all embodiments of this application including, but not limited to, steps in disclosed methods. Thus, if there are a variety of additional steps that may be performed it is understood that each of these additional steps may be performed with any specific embodiment or combination of embodiments of the disclosed methods.

The present methods and systems may be understood more readily by reference to the following detailed description of preferred embodiments and the examples included therein and to the Figures and their previous and following description.

As will be appreciated by one skilled in the art, the methods and systems may take the form of an entirely hardware embodiment, an entirely software embodiment, or an embodiment combining software and hardware embodiments. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including any non-transient computer-readable storage medium (e.g., hard disks, CD-ROMs, optical storage devices, and/or magnetic storage devices).

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, may be implemented by special purpose hardware-based computer systems that perform the specified functions or steps, or combinations of special purpose hardware and computer instructions.

In the following description, certain terminology is used to describe certain features of one or more embodiments. For purposes of the specification, unless otherwise specified, the term "substantially" refers to the complete or nearly complete extent or degree of an action, characteristic, property, state, structure, item, or result. For example, in one embodiment, an object that is "substantially" located within a housing would mean that the object is either completely within a housing or nearly completely within a housing. The exact allowable degree of deviation from absolute completeness may in some cases depend on the specific context. However, generally speaking, the nearness of completion will be so as to have the same overall result as if absolute and total completion were obtained. The use of "substantially" is also equally applicable when used in a negative connotation to refer to the complete or near complete lack of an action, characteristic, property, state, structure, item, or result.

As used herein, the terms "approximately" and "about" generally refer to a deviance of within 5% of the indicated number or range of numbers. In one embodiment, the term "approximately" and "about", may refer to a deviance of between 0.001-10% from the indicated number or range of numbers.

Various embodiments are now described with reference to the drawings. In the following description, for purposes of explanation, numerous specific details are set forth in order to provide a thorough understanding of one or more embodiments. It may be evident, however, that the various embodiments may be practiced without these specific details. In other instances, well-known structures and devices are shown in block diagram form to facilitate describing these embodiments.

FIG. 1 is a block diagram of an orientation sensor 30. The orientation sensor 30 (e.g., an absolute orientation sensor) may include an orientation sensing component 32 (e.g., a 6-axis inertial measurement unit (IMU), or an absolute orientation sensing component, such as a 9-axis IMU), a user input device 34, a processor 36, and/or a display 38. The orientation sensor 30 may include a memory 50, and/or a power source 52.

The user input device 34 may be operably coupled to the processor 36. For example, the user input device 34 may be configured to communicate a predetermined user input and/or other user inputs to the processor 36 and/or the memory 50. In an embodiment, the user input device includes a touchscreen display, a biometric interface, and/or a motion sensor. For example, the user input device may include one or more controls that allow the user to interact with and input information and/or commands to the orientation sensor and/or surgical instrument via the processor and/or the memory.

The orientation sensing component 32 may be configured to generate an absolute orientation by using the Earth itself as a reference point or plane, by sensing the Earth's magnetic field, and by extension, the Earth's magnetic core, rather than an arbitrarily determined point or plane. For example, the orientation sensing component 32 may include an accelerometer 60, a gyroscope 62, and a magnetometer 64. For example, when initially turned on the orientation sensing component 32 may generate an absolute orientation based upon an X-axis and a Y-axis that are perpendicular to one another and parallel to a horizontal plane planar with the surface of the Earth, and based upon a Z-axis (i.e., a vertical axis) that is perpendicular to the X-axis and the Y-axis. In an embodiment, when the orientation sensing component is activated (e.g., powered on or reset) the X-axis or the Y-axis is aligned with a predetermined portion of the orientation sensor (e.g., a longitudinal axis of the orientation sensor). In another embodiment, the X-axis or the Y-axis is colinear with a northward direction (e.g., magnetic north).

When the orientation sensor 30 is mounted to a surgical instrument (e.g., the impactor exemplified in FIG. 9) 100, the orientation of the orientation sensor 30 may be extrapolated to determine the orientation of the surgical instrument 100 (e.g., the orientation of a shaft 102 of the surgical instrument 100). At least part of the orientation of the surgical instrument 100 may be displayed with the display 38 such that a user can view the at least part of the orientation. For example, the display may be configured to display angles of inclination of the orientation sensor 30 relative to the Z-axis (e.g., as a vertical inclination angle) and the X-axis (e.g., as an anteversion angle). In an embodiment, orientation information and/or orientation data generated by the orientation sensing component is transmitted to an external electronic device (e.g., a display external to the surgical instrument).

The orientation sensor 30 is mountable to the surgical instrument 100. In an embodiment, the orientation sensor is mountable to substantially any surgical device.

The accelerometer 60 may be configured to measure linear acceleration. The accelerometer 60 may be a multi-axis accelerometer. When the accelerometer 60 is at rest relative to the surface of the Earth may measure a positive acceleration of 9.81 m/s, and when the accelerometer 60 is in free fall towards the center of the Earth the accelerometer 60 may measure an acceleration of 0 m/s.

The gyroscope 62 may include a spinning wheel or disc in which the axis of rotation is free to assume any orientation by itself, or may include a microelectrical mechanical system (MEMS). The gyroscope 62 may be configured to measure or maintain orientation, and/or provide information about angular acceleration, velocity, and/or position.

The magnetometer 64 may be configured to measure magnetism—including either magnetization of magnetic material like a ferromagnet, or the direction, strength, or the relative change of a magnetic field at a particular location. For example, the magnetometer 64 may be a multiaxial geomagnetic sensor.

The power source 52 may provide power to the orientation sensor 30, the device processor 36, and/or the display 38. The power source 52 may be a battery that is mechanically fixed relative to a body of the orientation sensor. In an embodiment, the power source is any other suitable component, such as a power source for the tool.

The processor 36 may be operatively coupled to, and control, the orientation sensor 30 and the display 38. In an embodiment, the orientation sensor includes an input/output device (e.g., transmitter/receiver) that is operably coupled to the processor 36.

The processor 36 may be, or may comprise, any suitable microprocessor or microcontroller. The processor 36 may be coupled (e.g., communicatively, operatively, etc.) to auxiliary devices or modules of the surgical instrument 100 using a bus or other coupling.

The orientation sensing component 32 may capture, in real-time, various orientation variables of the surgical instrument 100, including location, position (e.g., pitch, roll, and yaw) angular acceleration, velocity, linear acceleration. The orientation sensing component 32 may also capture, in real-time, magnetic field strength, gravity, and/or temperature. For example, the location of the surgical instrument 100 may include x, y, and z coordinate values, and other indicators of position and/or orientation in three-dimensional space.

The orientation sensor 30 may be configured to generate orientation information that is particular to the tool being used. For example, when the orientation sensor 30 is mounted on the surgical instrument 100, the orientation information generated by the orientation sensor 30 may include information associated with the location, the pitch, the roll, and/or the yaw of the tip, shaft 102, or active portion of the surgical instrument 100 (e.g., a drill portion of an awl, or another device or tool).

The orientation sensor 30 may be calibrated such that the orientation information generated by the orientation sensor 30 is based on the tip, shaft 102, or active portion of the surgical instrument 100 by the processor 36 calculating differences in orientation of the orientation sensor 30 and tip or active portion of the surgical instrument 100. For example, as discussed in more detail below, orientation information associated with a measured axis may be associated with a heading axis (e.g., a longitudinal axis) of the orientation sensor 30 and/or of the surgical instrument. In an embodiment, orientation information associated with more than one measured axis may be associated with respective axes of the orientation sensor and/or of the surgical instrument.

The orientation sensing component 32 may be configured to self-calibrate itself in relation to a horizontal plane and a vertical axis the Earth's magnetic field and/or the Earth's core as reference points or planes. For example, the orientation sensing component 32 may associate an X-axis and a Y-axis with a horizontal plane—e.g., parallel to a plane tangent to the Earth's surface—and a Z-axis with a vertical axis—e.g., parallel to an axis extending through the Earth's core.

The orientation sensing component 32 may be configured to generate orientation data comprising quaternion(s), Euler angle(s), rotation vector(s), linear acceleration(s), gravity, and/or a heading.

The orientation sensor 30, as discussed above, may be an absolute orientation sensor that may generate orientation values that are relative to the X-axis, the Y-axis, and/or the Z-axis. For example, the processor 36 may be configured to receive the orientation data from the orientation sensing component 32 and output orientation information to be displayed by the display. The orientation information may include data that represents a measured inclination relative to the X-axis, the Y-axis, and/or the Z-axis. For example, as discussed in more detail below, the orientation information may include data that represents a measured inclination relative to a user-identified X-axis, the Y-axis perpendicular to the X-axis, and the Z-axis perpendicular to the X-axis and the Y-axis. The orientation information may include data that represents a measured rotation (e.g., synchronous rotation) relative to the Y-axis, a measured rotation (e.g., synchronous rotation) relative to the Z-axis, and/or a measured rotation (e.g., synchronous rotation) relative to the X-axis.

In an embodiment, the orientation information includes data representing all of the measured orientation data in relation to the X-axis, the Y-axis, and/or the Z-axis. In other embodiments, the orientation information includes data representing any combination of the measured orientation data in relation to the X-axis, the Y-axis, and/or the Z-axis.

Movement of the surgical instrument may result in the display displaying the orientation information in real-time. For example, the rotation about the X-axis, the Y-axis, and/or the Z-axis may be displayed in real-time by the display 38—with or without an adjustment depending on the particular tool or type of procedure. As discussed in more detail below, the rotation about the Y-axis may be displayed as an anteversion angle of the tool and the rotation about the Z-axis may be displayed as an inclination angle of the tool.

The display may be visible by the user (e.g., a surgeon) during use (e.g., during a surgery). For example, the display may be configured to display the orientation data to for a surgeon to view when the angle of the tool is not easily discernable by the surgeon. The display provides for the surgeon to discern the precise orientation of the tool when the tool is at least partially inside the patient, even when a significant portion of the tool is not visible to the surgeon.

The processor 36 may transmit a signal comprising the orientation information to the display 38. The display 38 may digitally display orientation values that represent the orientation information such that the user may read the orientation values on the display 38. In an embodiment, the display is configured to display the orientation values at a location remote from the body of the orientation sensor 30 and the tool. For example, the input/output device may transmit the orientation information to an external display (e.g., a monitor mounted on a wall in the surgical room).

In some embodiments, the display or another display is configured to display a predetermined light signal when a predetermined orientation condition of the tool (e.g., a predetermined rotation about one of the axes) is met. The color or intensity of the light signal may be based on how far the tool is outside and/or inside the predetermined orientation condition.

In some embodiments, in addition to or alternatively to the display an audio device is configured to generate a sound when a predetermined orientation condition of the tool (e.g., a predetermined rotation about one of the axes) is met. The type or intensity of the sound may be based on how far the tool is outside and/or inside the predetermined orientation condition.

Figure 2:
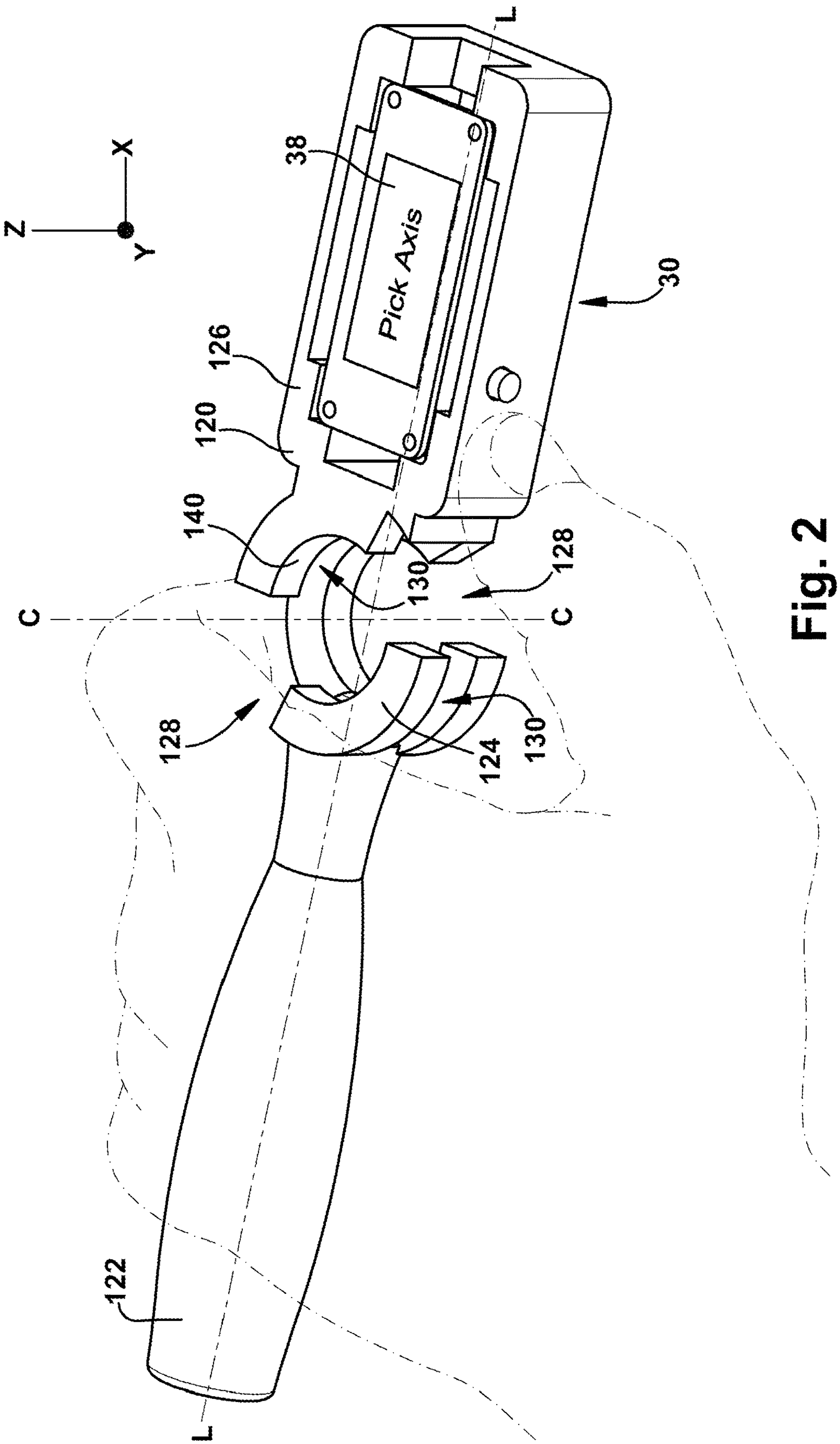
FIG. 2 is an oblique view of the orientation sensor of FIG. 1.
Figure 3:
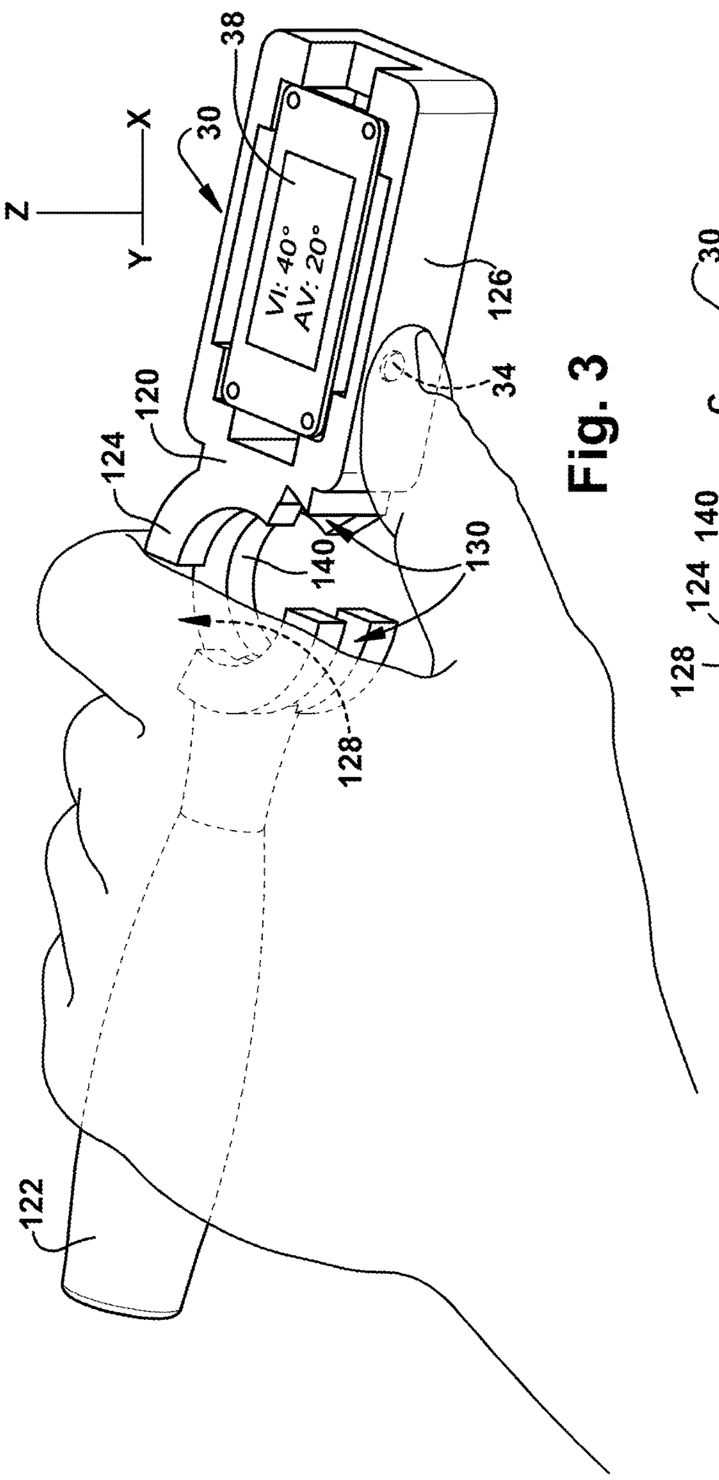
FIG. 3 is an oblique view of the orientation sensor of FIG. 1 while a heading is being set.
Figure 4:
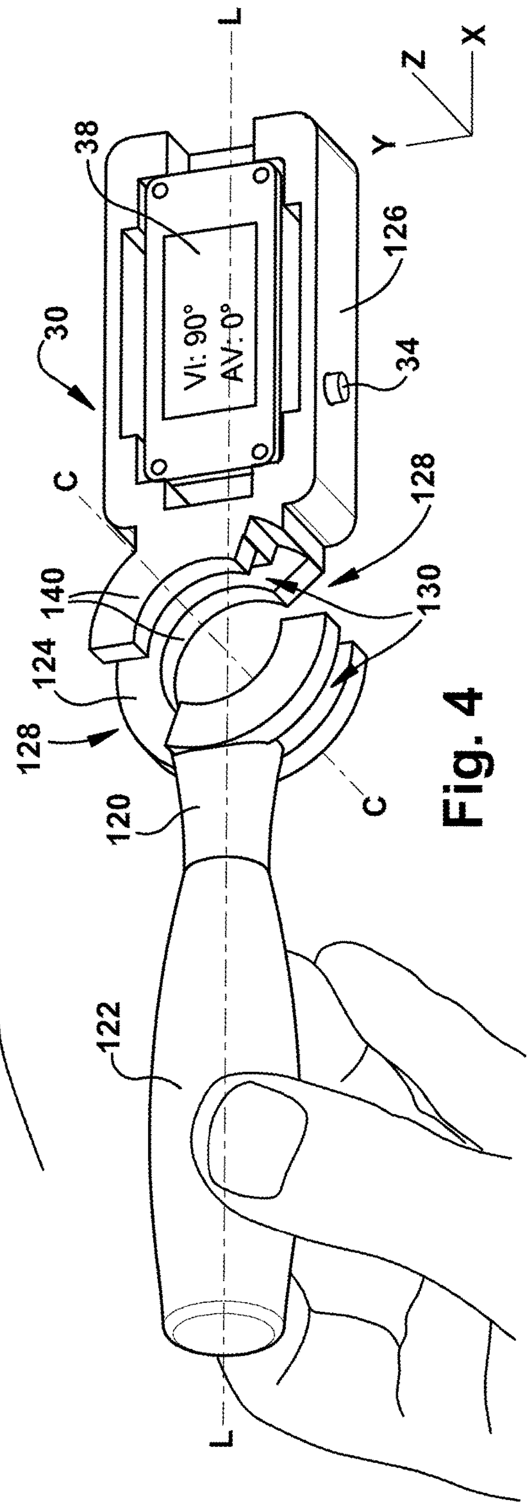
FIG. 4 is an oblique view of the orientation sensor of FIG. 1 after a heading has been set and the orientation sensor is oriented to a predetermined reference orientation relative to the heading.
Figure 9:
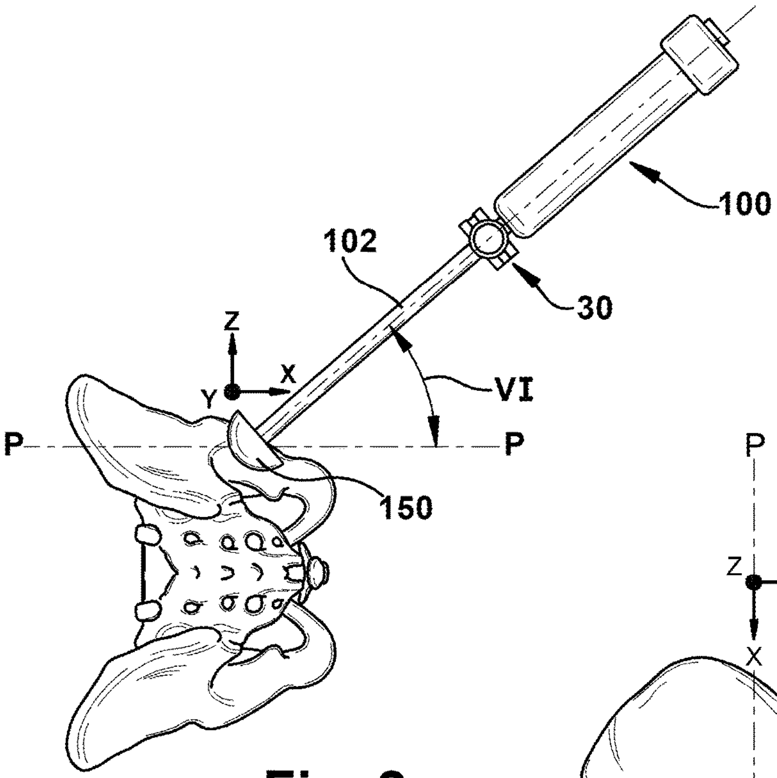
FIG. 9 is a posterior to anterior view of the pelvis in combination with the orientation sensor of FIG. 7 and a surgical instrument.

FIGS. 2-4 illustrate an example of the orientation sensor 30 that is configured to receive a part of the tool (e.g., the shaft 102 of the impactor, as exemplified in FIG. 9). The orientation sensor may include a sensor body 120. The sensor body 120 may define a handle 122, a guide 124, and/or a display arm 126.

The display 38 may be mounted to the display arm 126. For example, the display 38 may be oriented to face in a display direction perpendicular to a longitudinal sensor body axis L. As discussed above, the display 38 portion may display the current orientation of the orientation sensor 30 (e.g., within a hundredth of a second in real-time).

The handle 122 may be configured to be held in the hand of a surgeon. For example, the handle 122 may be elongate along the longitudinal sensor body axis L. In an embodiment, the handle includes at least some of the electronical components of the orientation sensor. For example, the handle may include the processor, the user input device, the orientation sensing component, and/or the power source.

The display arm 126 may be elongate along the longitudinal sensor body axis L. The display arm 126 may be fixed relative to the handle 122 and/or at least part of the guide 124. In some embodiments, the display arm is configured to move relative to the handle. For example, in an embodiment, the display arm is rotatable about one or more axes (e.g., a lateral axis that is transverse to the longitudinal sensor body axis) relative to the handle as discussed in U.S. patent application Ser. No. 16/395,986 filed on Apr. 26, 2019.

The display arm 126 may include at least some of the electronical components of the orientation sensor. For example, the display arm 126 may include the processor 36, the user input device 34, the orientation sensing component 32, the power source 52, and/or the display 38 (shown in FIG. 1). In an embodiment, any of or any combination of the processor, the user input device, the orientation sensing component, the power source, and/or the display is mounted to another component of the orientation sensor.

The guide 124 may be fixed relative to the handle 122. The guide 124 may be configured to mount to the tool 100 (e.g., the shaft 102 of the impactor). For example, the guide 124 may be configured to receive the shaft 102 and/or attach to the tool 100. In some embodiments, the guide or another portion of the orientation sensor is a different shape to mount to a different surgical tool.

When mounted, the guide 124 may substantially circumscribe a portion of the shaft 102. For example, the guide 124 may include lateral opening (e.g., to receive the shaft 102 of the tool 100 in a lateral direction). In an embodiment, the guide entirely circumscribes a portion of the shaft when mounted.

A radially outer portion of the guide 124 may include one or more longitudinally extending notches 128, along a central guide axis C of the guide 124, that connect to a respective circumferentially extending slot 130. The circumferentially extending slot 130 may be open at only one circumferential end such that the other circumferential end is formed by a wall.

As shown in FIGS. 2-4 the inner surfaces 140 of the guide 124 may curved about the central guide axis C. The central guide axis C may be colinear or parallel with the shaft 102 of the tool 100 when the guide 124 is mounted to the tool 100. For example, each inner surface 140 may conform to a generally cylindrical shape (e.g., the shaft 102 of the impactor).

When the tool 100 is in a mounted position in the guide 124, the guide 124 and/or the sensor body 120 may be only rotatable about the shaft 102 of the tool 100. The user may manually restrain relative movement of the guide 124 and the tool 100 by holding the handle 122 of the orientation sensor 30 and the handle 122 of the tool 100 together (e.g., with a single hand). In an embodiment, the guide is configured to be entirely fixed relative to the impactor when the guide is mounted to the impactor such movement of the guide relative to the impactor in every direction is prevented.

The absolute orientation sensing component 32 may be configured to be removable from the instrument body by hand. For example, the entire orientation sensor 30 may be rotated from the mounted position relative to the impactor and removed from the impactor shaft by hand (i.e., without a tool) by sliding and/or laterally moving the shaft through an opening of the guide 124.

In an embodiment, the guide includes a bearing that is configured to slide and/or rotated about a shaft of the tool. For example, the bearing may include an inner cylinder that is configured to rotate relative to and outer cylinder separated from the inner cylinder by ball bearings. In some embodiments, the guide includes a cylindrical bushing that is i) disposed within an outer guide body that is fixed relative to the handle, and ii) configured to slide and/or rotate about a shaft of the tool.

Figure 10:
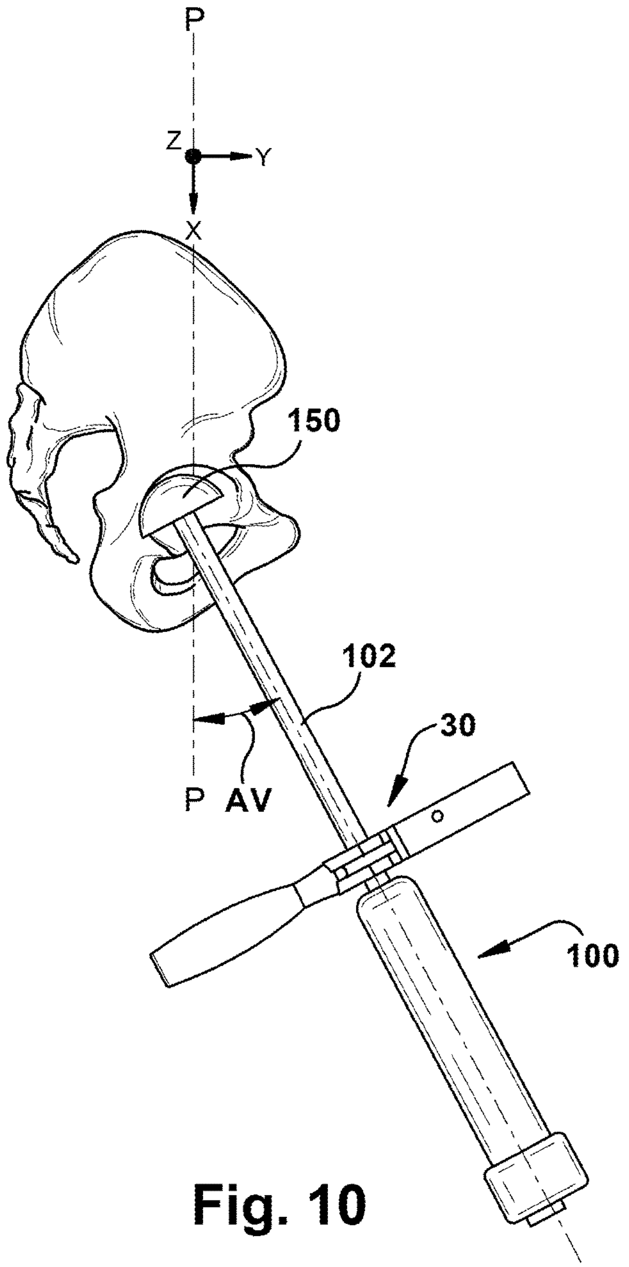
FIG. 10 is a lateral view of the pelvis in combination with the orientation sensor and the surgical instrument of FIG. 9.

FIGS. 9 and 10 illustrates the orientation sensor 30 in combination with the tool 100. As discussed above, the guide 124 may be configured to laterally receive the shaft 102 of the impactor relative to the central guide axis C and/or configured to longitudinally slide along the shaft 102. In an embodiment, the tool is an awl, a tap, or a screwdriver and the guide is configured receive the shaft of the awl, the tap, and/or the screwdriver and slide longitudinally along the corresponding shaft (e.g., until a handle of the awl abuts the orientation sensor). In some embodiments, the same orientation sensor is configured to mount to the shaft of the impactor, the awl, the tap, and/or the screwdriver.

The user input device 34 may be positioned on the display arm 126 such that a user gripping the handle 122 in the palm of one of the user's hands would be able to touch the user input device 34 with the thumb of the hand gripping the handle 122. For example, the user input device 34 may be disposed on a side of the display arm 126 at an end of the display arm 126 that is adjacent the guide 124.

As shown in FIGS. 9 and 10, the tool 100 may comprise a handle 122 and the shaft 102. An end of the shaft 102 opposite the handle 122 may be configured to hold an acetabular cup 150. For example, the end of the shaft 102 may be configured to expand to hold the acetabular cup 150, and configured to contract to release the acetabular cup 150.

In an embodiment, the orientation sensor is attachable to/detachable from or permanently integrated into the tool or another device, such as a surgical/medical device/equipment.

Turning to FIGS. 5-8, an example of setting a heading based on the orientation of the orientation sensor is represented. The processor 36 may be configured to, in response to the user input device 34 receiving the predetermined user input, set the heading based on the orientation of the orientation sensor 30 when the predetermined user input is received by the user input device 34.

Figure 5:
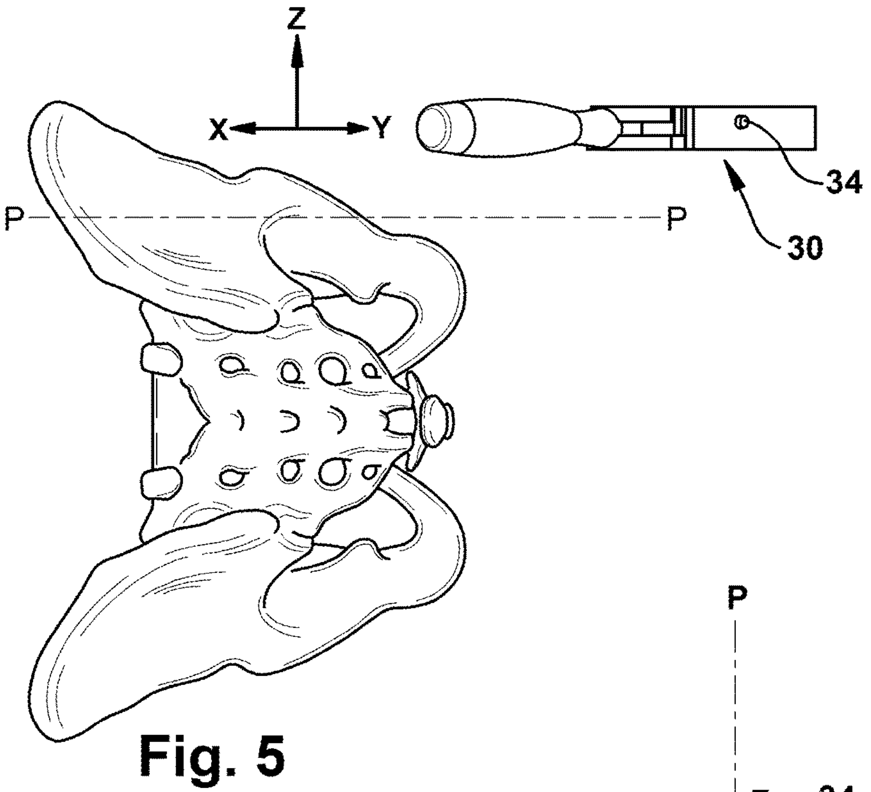
FIG. 5 is a posterior to anterior view of a pelvis in combination with the orientation sensor of FIG. 1 with an arbitrary heading.
Figure 6:
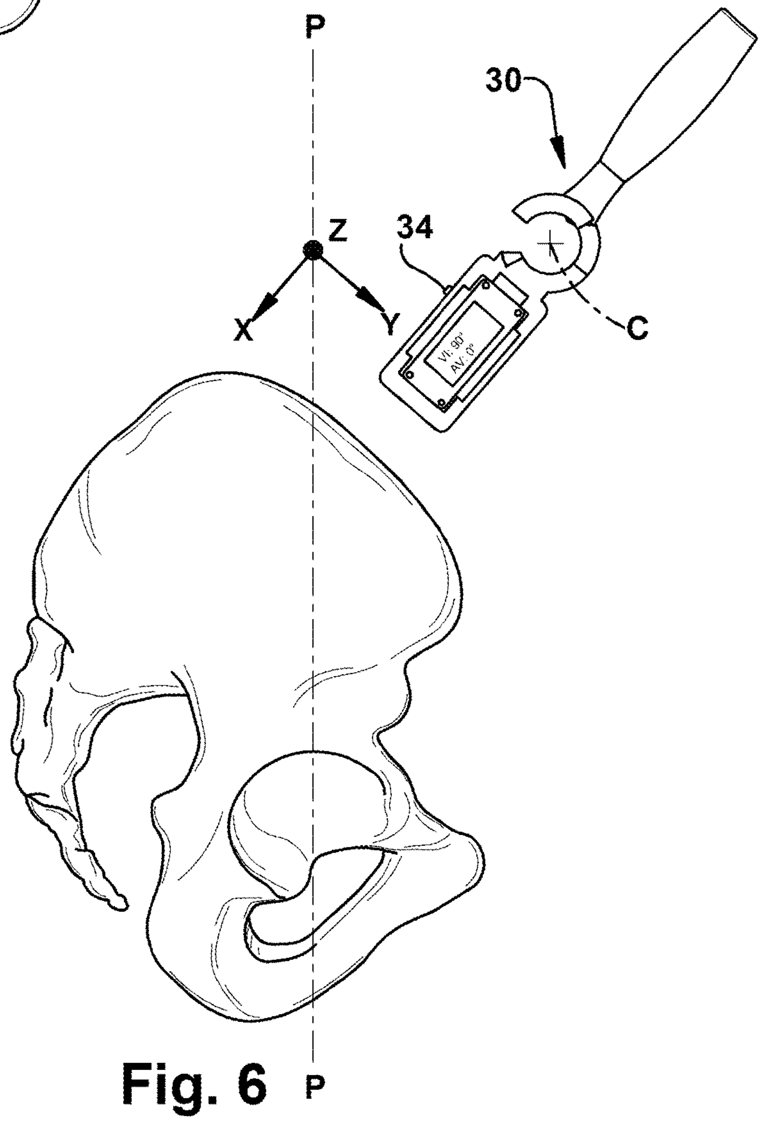
FIG. 6 is a lateral view of the pelvis in combination with the orientation sensor of FIG. 5.
Figure 7:
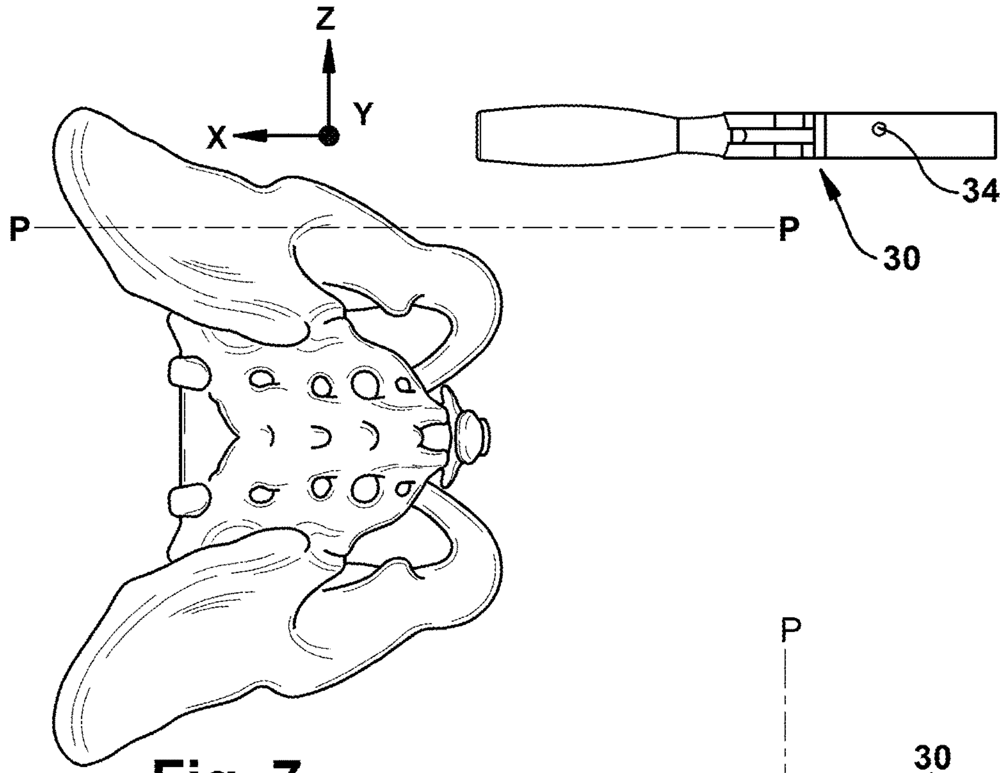
FIG. 7 is a posterior to anterior view of the pelvis in combination with the orientation sensor of FIG. 5 with a user-identified heading.
Figure 8:
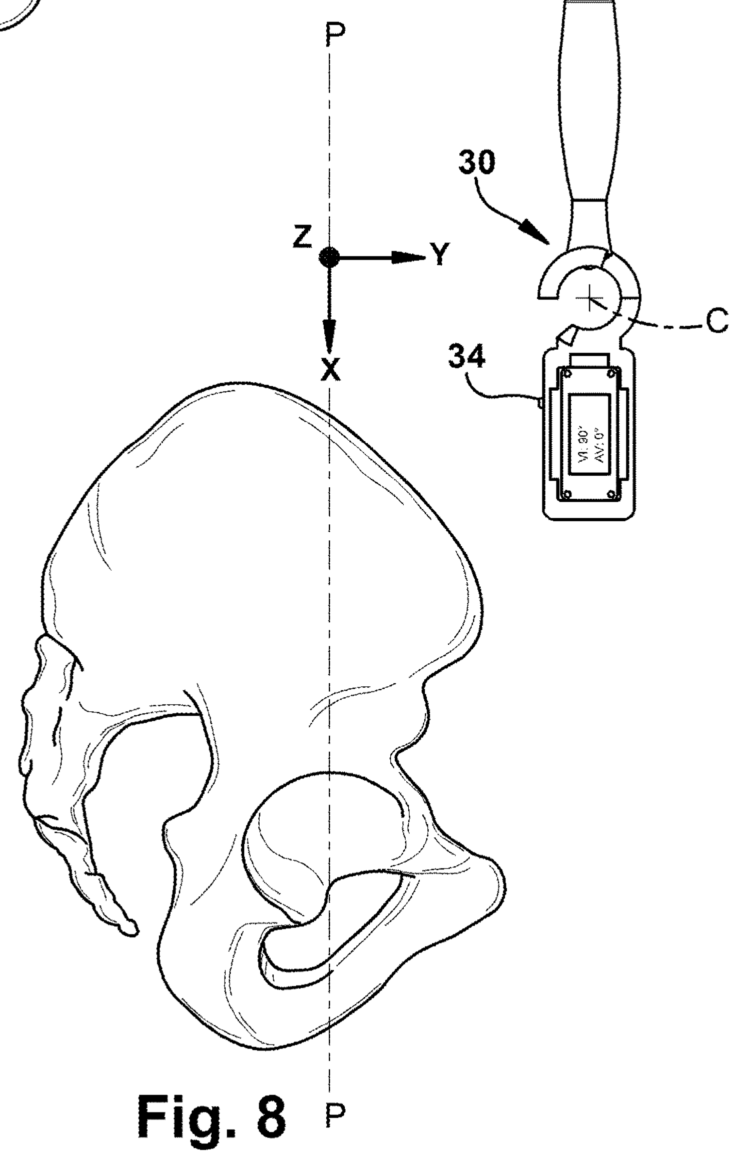
FIG. 8 is a lateral view of the pelvis in combination with the orientation sensor of FIG. 7.

The processor 36 may be to configured to associate the heading with a predetermined axis relative to the orientation sensor when the user presses the button. For example, when the heading is initially set to an undesired and arbitrary X-axis, as shown in FIGS. 5 and 6, that is not aligned with a desired axis (e.g., the longitudinal body axis P of the patient), the heading may be re-set to align or be associated with the longitudinal body axis P of the patient, as shown in FIGS. 7 and 8. The orientation of the X-axis (e.g., relative to the Earth) may not change based upon changing of the orientation of the orientation sensor 30 alone. Rather, the predefined user input (e.g., pressing the button) may cause the re-orientation of the coordinate system (e.g., associating the X-axis to the new heading).

The processor 36 may associate set the new heading by rotating the X-axis and the Y-axis about the Z-axis (e.g., the yaw axis) until the X-axis aligns with a plane defined by the Z-axis and the longitudinal sensor body axis L of the orientation sensor 30 (e.g., the processor is configured to zero rotation about the yaw axis). For example, as shown in FIGS. 7 and 8, the longitudinal sensor body axis L of the orientation sensor 30 may be aligned with the longitudinal body axis P of the patient (e.g., of the patient's pelvis), and while aligned the button 34 may be pressed, which causes the processor 36 to set the new heading by aligning the X-axis with the longitudinal sensor body axis L of the orientation sensor 30, thereby aligning the X-axis with the longitudinal body axis. The processor 36 may rotate the X-axis and the Y-axis about the Z-axis until the X-axis aligns with the longitudinal sensor body axis L to set the heading. After the heading is set, the heading may not change until the orientation sensor 30 is reset (e.g., by receiving additional user input, or by deactivating and reactivating the orientation sensor 30).

If the longitudinal axis is inclined relative to the X-Y plane (e.g., rotated about a pitch axis), the X-axis may be aligned with the longitudinal sensor body axis L such that the longitudinal axis maintains the inclination relative to the X-Y plane and is in the X-Z plane. Accordingly, if the X-Y plane represents a horizontal plane relative to the Earth prior to the heading being set, the X-Y plane continues to represent the horizontal plane after the heading is associated with the longitudinal sensor body axis L, even if the longitudinal axis is inclined relative to the horizonal plane.

When orientation sensor 30 is activated, the display 38 may indicate that a heading or axis needs to be chosen by the user. The processor 36 may be configured to receive the predetermined user input when the indication is present. For example, the display 38 may display the prompt "pick axis," and the processor 36 may be configured to receive the predetermined user input from the user pressing the button 34 when the prompt is displayed. In an embodiment, the heading may be set each time the predetermined user input is received.

The processor 36 may be configured to store the heading in the memory 50 in response to receiving the predetermined user input. The processor 36 may be configured to generate the orientation information based on the heading, that is stored in the memory 50, and the current orientation of the orientation sensor. As discussed below in relation to the orientations shown in FIGS. 11-14, the orientation sensor 30 does not need to be held flat in the orientation shown in FIG. 8—such that the central guide axis C is parallel with the Z-axis—to align the heading with the longitudinal body axis P.

Figure 15:
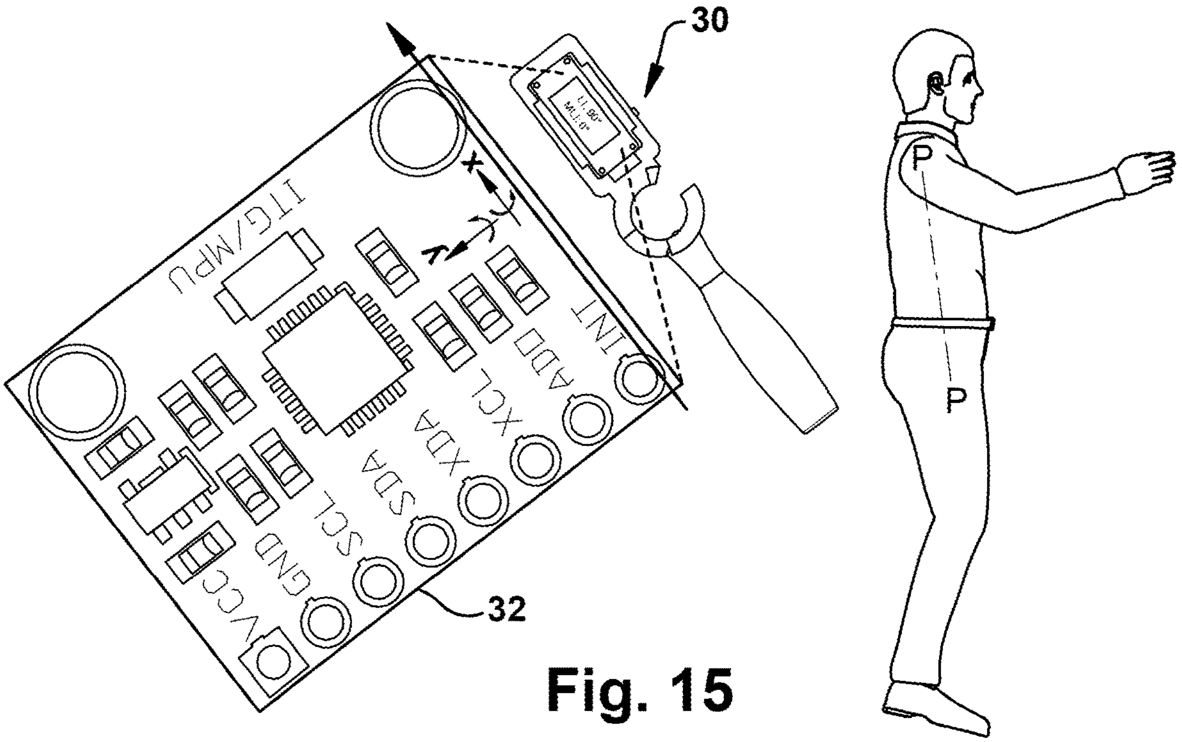
FIG. 15 is a top view of the orientation sensor of FIG. 1, with an arbitrary heading, in relation to an orientation sensing component of the orientation sensor and a longitudinal body axis of a patient lying on their side.

The heading may be associated with the orientation data such that when the orientation sensor 30 would be held in a predetermined reference orientation relative to the heading, the processor 36 generates predetermined orientation information and the display 38 displays a predetermined orientation value. For example, if the central guide axis C is entirely vertical (e.g., colinear or parallel with the Z-axis), processor may generate the predetermined orientation information such that the display 38 may display one or more predetermined angular values (e.g., a vertical inclination angle of 90° and an anteversion angle of 0° as shown in FIG. 8, or a longitudinal inclination angle of 90° and a medial-lateral inclination angle of 0° as shown in FIG. 15). If the orientation sensor is rotated from the predetermined reference orientation about the Y-axis (e.g., the pitch axis) by 45°, the display may display a vertical inclination angle of 45° (or a longitudinal inclination angle of 45°). If the orientation sensor 30 is further rotated about the Z-axis (e.g., the yaw axis) by 15° (e.g., such that the central guide axis C is inclined by 15° from the X-Z plane), the display may display an anteversion angle of 15° (or a medial-lateral inclination angle of 15°). Accordingly, changing the orientation of the orientation sensor, may result in a change in one or more of the orientation values displayed by the display 38. The displayed values may remain the same (e.g., may not change in value) regardless of whether the orientation sensor 30 is rotated about the central guide axis C from a given position.

Turning to FIGS. 9 and 10, the orientation sensor 30 may be mounted to the shaft 102 (an example of an instrument body, or a portion of an instrument body) of the tool 100 such that the orientation sensor is at least partially fixed to the shaft 102. When the tool 100 is holding the acetabular cup 150 in a desired location of the pelvis, the heading has been set to the longitudinal body axis P of the patient, and the patient is lying on their side, the display 38 may display the vertical inclination and anteversion angles based on the orientation of the tool 100. For example, as the tool 100 is rotated about the Y-axis, as shown in FIG. 9, the display 38 may display the vertical inclination angle (or a longitudinal inclination angle) in real-time (e.g., 40° in the orientation shown in FIG. 9). As the tool 100 is inclined from the X-Z plane or rotated relative to the Z-axis, the display 38 may display the anteversion angle (or a medial-lateral inclination angle) in real-time (e.g., 15° in the orientation shown in FIG. 10). As discussed below, the heading may be set to an axis other than the longitudinal body axis P.

Turning to FIGS. 11-14, the orientation sensor 30 is illustrated in two different positions that may result in the same heading, as discussed above, when the button is pressed by the user (an example of the user input). For example, in FIG. 4 above, the longitudinal sensor body axis L and the display 38 are coplanar with a horizontal plane such that the display 38 faces in a direction along the Z-axis. When in this orientation, pressing the user input device 34 may set the heading by causing the processor 36 to align the X-axis with the horizontal component of the longitudinal sensor body axis L. The X-axis and the Y-axis may be rotated about the Z-axis until the X-axis aligns with the horizontal component of the longitudinal sensor body axis L (e.g., by saving the heading—e.g., at least the rotation about the Z-axis—in the memory 50).

Figure 11:
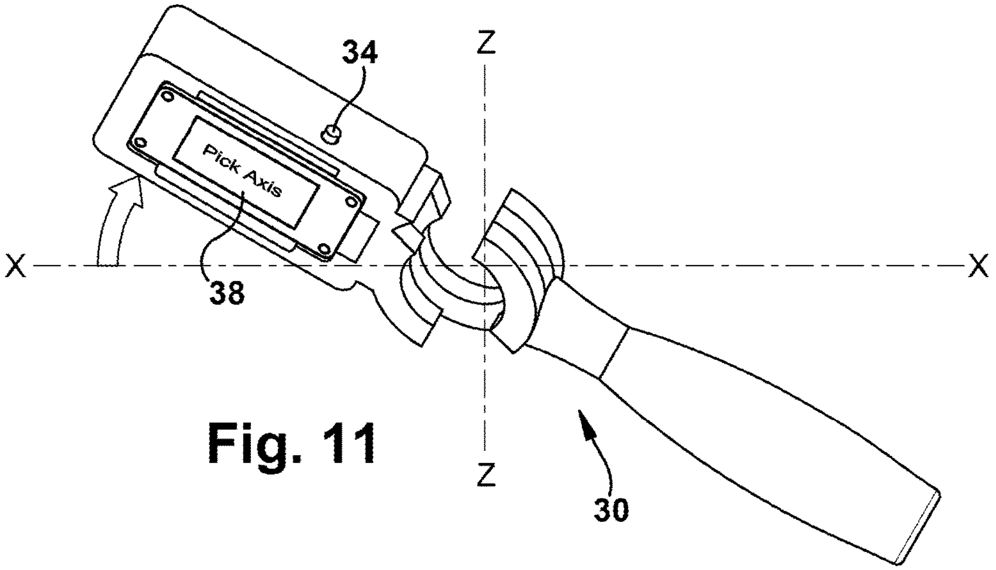
FIG. 11 is a side view of the orientation sensor of FIG. 1 in which the longitudinal sensor body axis of the orientation sensor is rotated about the X-axis, inclined relative to an X-axis and a Z-axis, and extends entirely in an X-Z plane.
Figure 12:
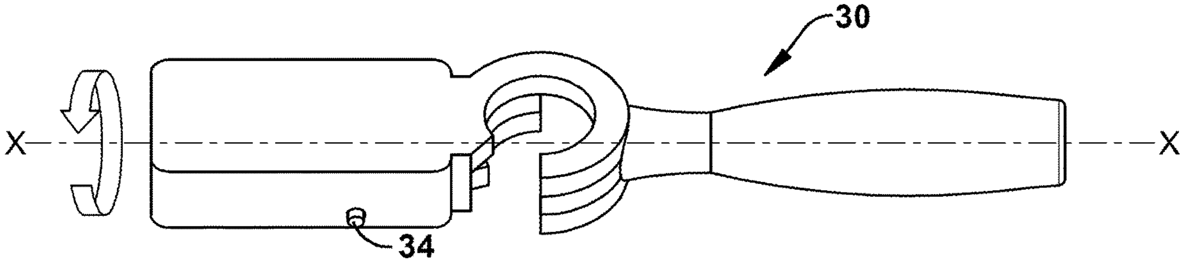
FIG. 12 is a top view of the orientation sensor in the orientation shown in FIG. 11.
Figure 13:
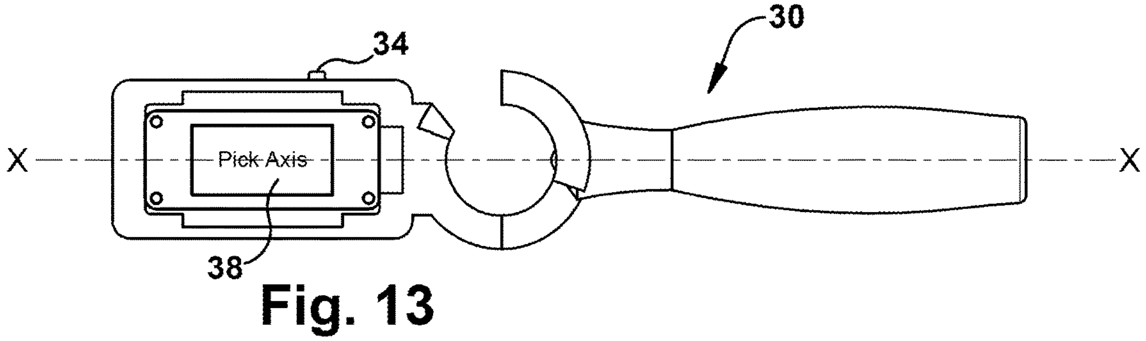
FIG. 13 is a side view of the orientation sensor of FIG. 11 in which the longitudinal sensor body axis of the orientation sensor is rotated about the X-axis from the orientation shown in FIG. 11, not inclined relative to an X-axis, and extends entirely in an X-Z plane.
Figure 14:
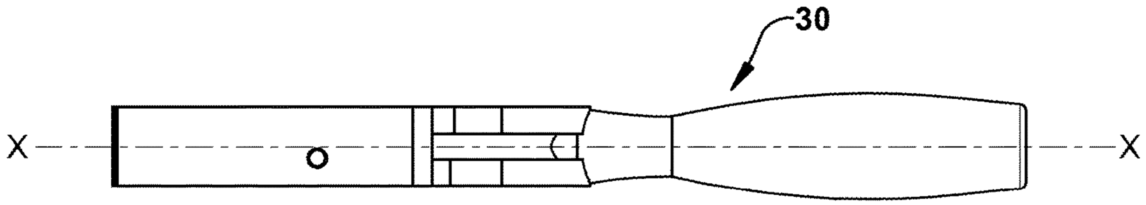
FIG. 14 a top view of the orientation sensor in the orientation shown in FIG. 13.

On the other hand, in FIGS. 11 and 12 the longitudinal sensor body axis L has been rotated relative to the X-axis, inclined relative to the X-axis and the Z-axis, and, similar to FIG. 4, extends entirely in the X-Z plane. In FIGS. 13 and 14, the longitudinal body axis L is rotated about the X-axis so that the display faces in a direction along the Y-axis, is not inclined relative to the X-axis, and extends entirely in the X-Z plane. Similar to the orientation shown in FIG. 4, when in the orientations shown in FIGS. 11-14, pressing the user input device 34 may set the heading by causing the processor 36 to align the X-axis with the horizontal component of the longitudinal sensor body axis L. The X-axis and the Y-axis may be rotated about the Z-axis until the X-axis aligns with the horizontal component of the longitudinal sensor body axis L (e.g., by saving the heading—e.g., at least or only the rotation about the Z-axis—in the memory 50).

Accordingly, in relation to a patient (e.g., lying in the position shown in FIG. 15) the orientation sensor 30 may be held in any of the positions shown in FIG. 4 or 11-14 such that the longitudinal sensor body axis L extends entirely in a plane defined by the desired axis of the patient (e.g., the longitudinal body axis P) and the vertical axis (e.g., the Z-axis). Pressing the user input device 34 when the longitudinal sensor body axis L extends entirely in the plane defined by the desired axis and the vertical axis (e.g., in any of the positions shown in FIG. 4 or 11-14), may cause the processor 36 to align the X-axis with such plane. For example, by keeping the X-axis at its current alignment shown in FIGS. 11-14, if the heading is already set to the direction shown in FIGS. 11-14 (e.g., the orientation of the X-axis). If, instead, the heading was previously set to a different direction than shown in FIGS. 11-14 (e.g., if the X-axis is aligned in a different direction relative to the orientation sensor 30), pressing the user input device 34 while the orientation sensor is in any of the orientations shown in FIGS. 11-14 may cause the processor 36 to rotate the X-axis and the Y-axis about the Z-axis until the X-axis aligns with the plane defined by the by the desired axis and the vertical axis (e.g., by saving the heading—e.g., at least or only the rotation about the Z-axis—in the memory 50).

Figure 16:
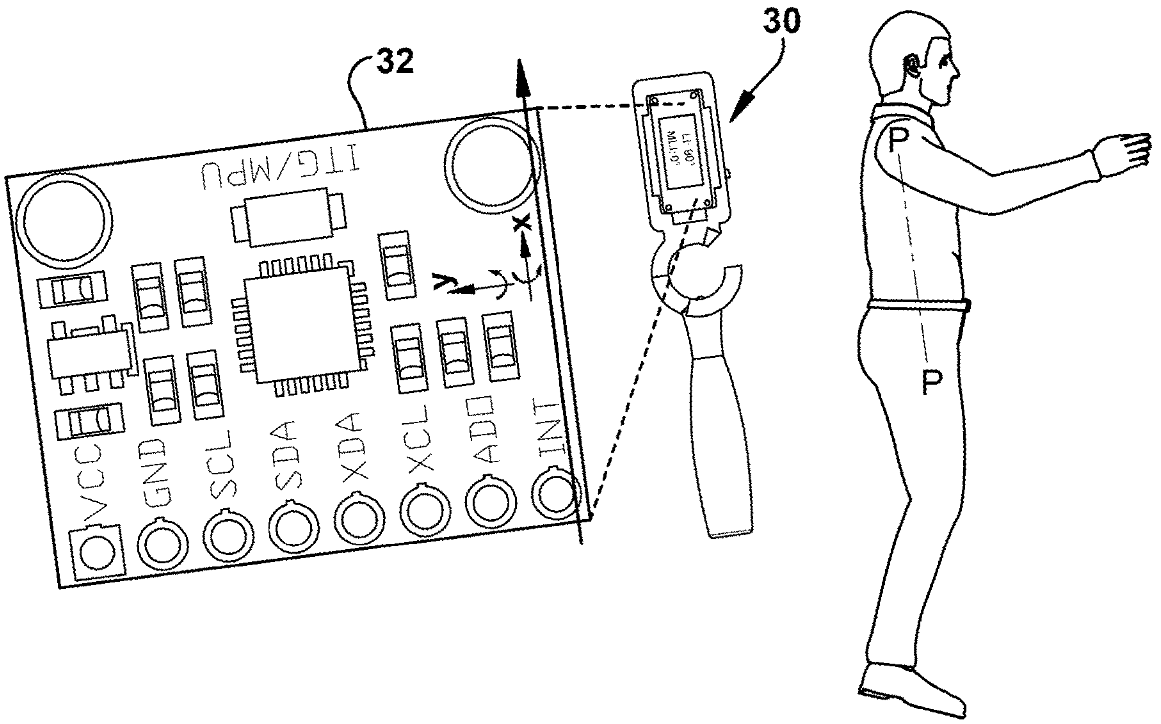
FIG. 16 is a top view of the orientation sensor, with user-identified heading, in relation to the orientation sensing component and the longitudinal body axis FIG. 15.

FIGS. 15-21 provide other representative examples of headings that the orientation sensor may be set to in relation to the orientation of the IMU 32 of the orientation sensor 30. The orientation of the IMU 32 relative to the orientation of the orientation sensor 30 is exemplified in FIGS. 15-21 (as discussed above, the IMU 32 may be disposed within the body of the orientation sensor 30, as represented by dashed lines in FIGS. 15-21). FIGS. 15 and 16 illustrate a patient that is lying on their side with the longitudinal body axis P extending from their shoulder to their hip. As discussed above, the orientation sensor may have a heading set in a direction that is undesirably misaligned with the longitudinal body axis P, as exemplified with the arrow along the IMU in FIG. 15. The heading of the orientation sensor may be set to the longitudinal body axis by aligning the longitudinal sensor body axis L of the orientation sensor 30 with the longitudinal body axis, as shown in FIG. 16, and then providing the predetermined user input to the user input device 34.

Figure 17:
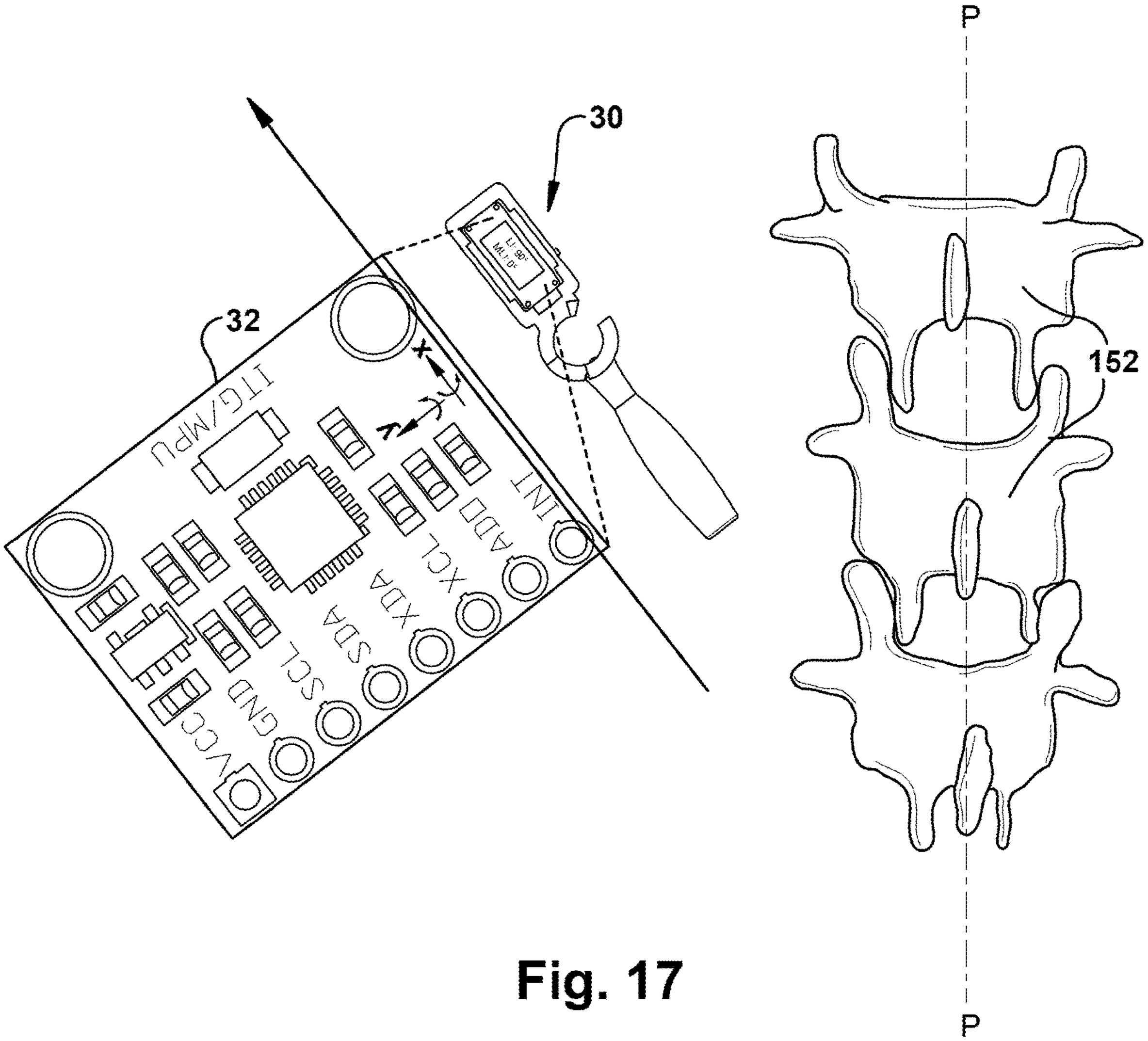
FIG. 17 is a top view of the orientation sensor of FIG. 1, with an arbitrary heading, in relation to an orientation sensing component of the orientation sensor and a longitudinal body axis of a patient's spinous process.
Figure 18:
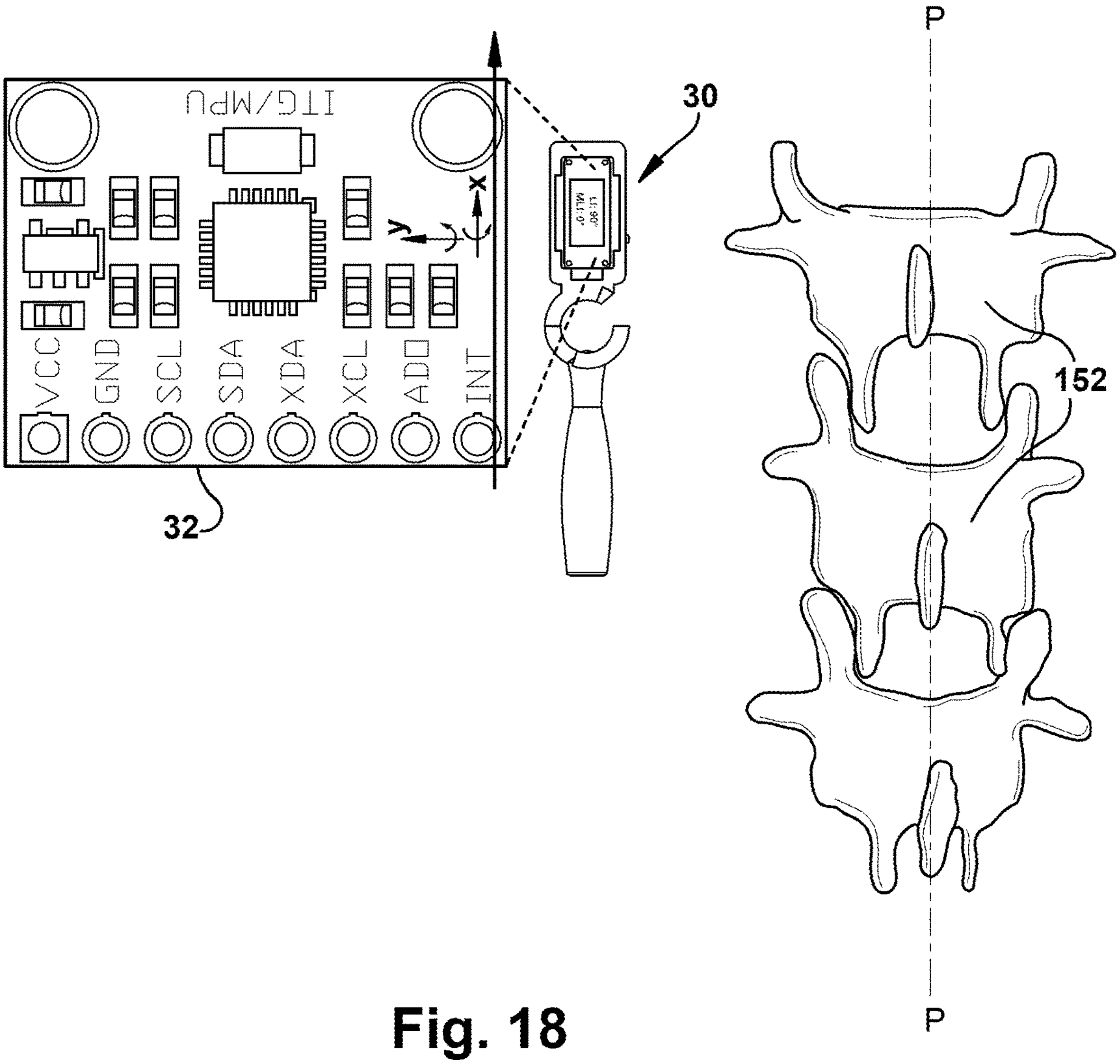
FIG. 18 is a top view of the orientation sensor, with user-identified heading, in relation to the orientation sensing component and the longitudinal body axis FIG. 17.

FIGS. 17 and 18 illustrate multiple vertebrae 152 of a patient. The desired longitudinal body axis may extend along one or more of the spinous processes of the vertebrae. Similar to the above, the orientation sensor may have a heading set in a direction that is undesirably misaligned with the longitudinal body axis P, as exemplified with the arrow along the IMU in FIG. 17. The heading of the orientation sensor may be set to the longitudinal body axis by aligning the longitudinal sensor body axis L of the orientation sensor 30 with the longitudinal body axis, as shown in FIG. 18, and then providing the predetermined user input to the user input device 34. In an embodiment, the longitudinal body axis extends along a center of the vertebral bodies of the patient.

Figure 19:
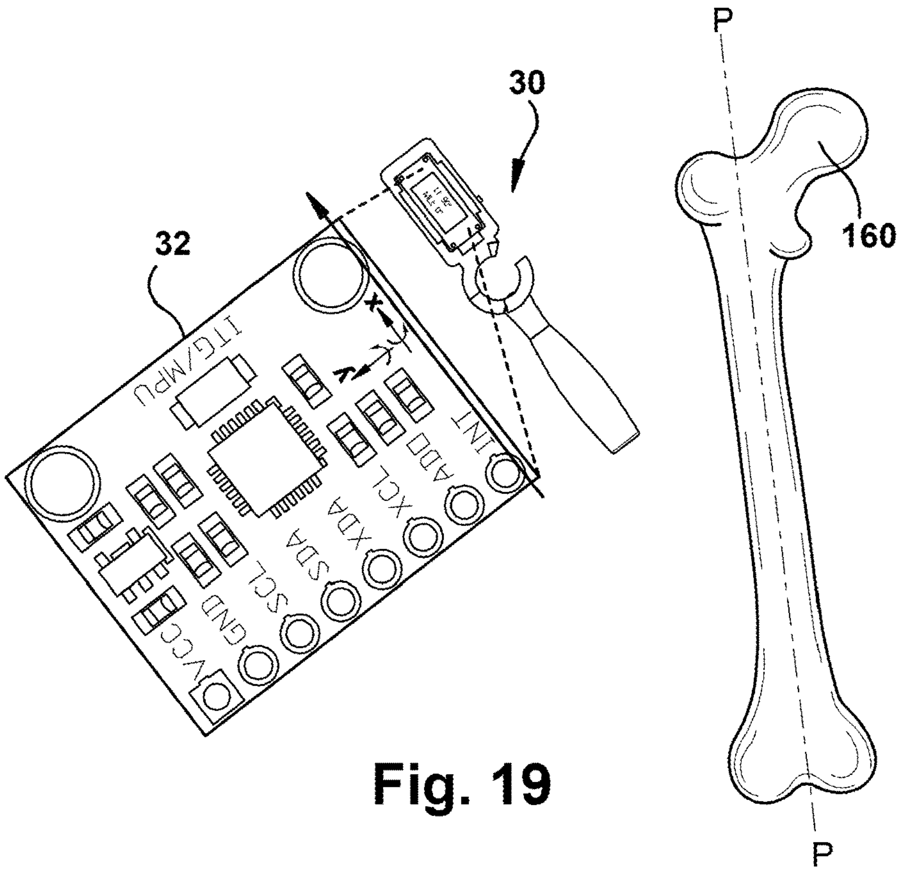
FIG. 19 is a top view of the orientation sensor of FIG. 1, with an arbitrary heading, in relation to an orientation sensing component of the orientation sensor and a longitudinal body axis of a patient's bone.
Figure 20:
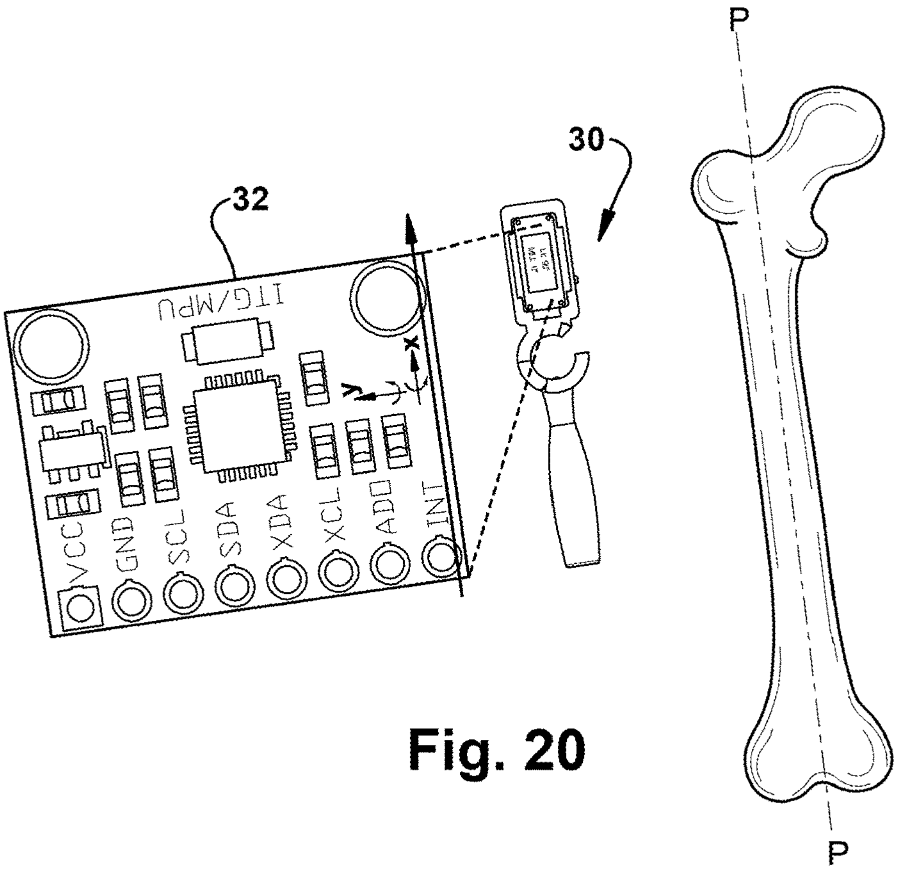
FIG. 20 is a top view of the orientation sensor, with user-identified heading, in relation to the orientation sensing component and the longitudinal body axis FIG. 19.
Figure 21:
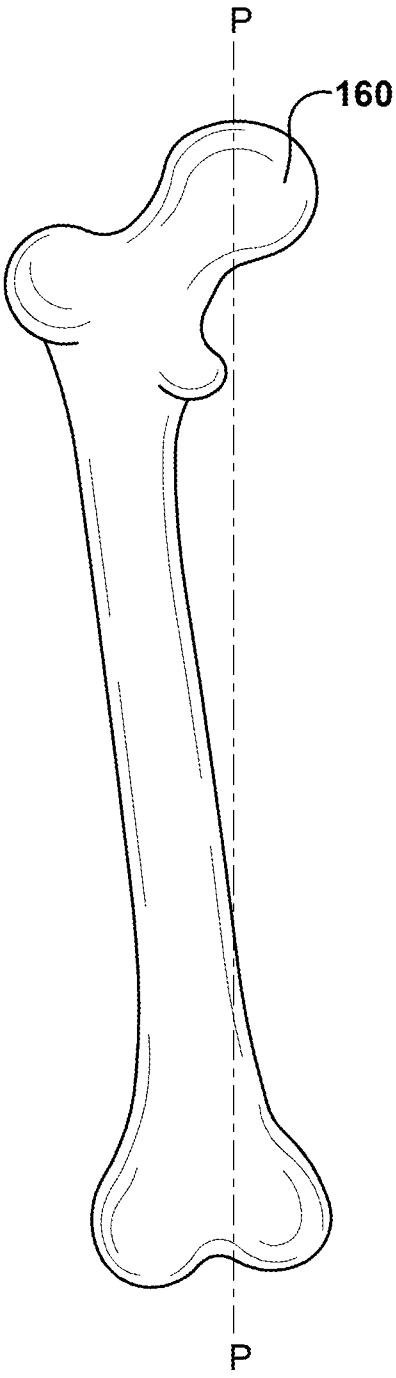
FIG. 21 is top view of the patient's bone of FIG. 19 with an alternative longitudinal body axis.

FIGS. 19-21 illustrate a bone 160 of a patient. The desired longitudinal body axis may extend along the anatomical axis of the bone 160, as shown in FIGS. 19 and 20, or may extend along the mechanical axis of the bone 160, as shown in FIG. 21. Similar to the above, the orientation sensor 30 may have a heading set in a direction that is undesirably misaligned with the longitudinal body axis P, as exemplified with the arrow along the IMU in FIG. 19. The heading of the orientation sensor may be set to the longitudinal body axis by aligning the longitudinal sensor body axis L of the orientation sensor 30 with the desired longitudinal body axis P, as shown in FIG. 20, or in a similar manner for the longitudinal body axis of FIG. 21, and then providing the predetermined user input to the user input device 34.

The processor 36 may be configured to determine whether the orientation of the orientation sensor is within a predetermined threshold of a predetermined alignment orientation. For example, the predetermined alignment orientation may include a vertical inclination of 40° relative to the X-Y plane and includes an anteversion angle of 15° relative to the X-Z plane. The threshold for each value may be +/−10°. Accordingly, if the vertical inclination of the orientation sensor 30 is anywhere from 30° to 50° and/or the anteversion angle of the orientation sensor 30 is anywhere from 5° to 25°, the processor 36 may determined that the orientation is within the predetermined threshold of the predetermined alignment orientation.

In some embodiments, the button 34 is configured to change modes of the orientation sensor 30 from a first mode to a second, and/or vice versa. For example, as discussed below with reference to FIGS. 22-26C, in the first mode the display 38 may be configured to display a first vertical inclination angle and a first anteversion angle of an impactor shaft relative to a surgical patient in a lateral position, and in the second mode the display 38 may be configured to display a second vertical inclination angle and a second anteversion angle relative to a patient in a supine position. The display 38 may be configured to indicate the current mode of the device (e.g., displaying "lateral" or "supine"). In some embodiments, the user may press the button 34 in response to a prompt indicating the user should select the mode to change the current mode of the orientation sensor.

In an embodiment, the one or more lights of the light source turn on/off or pulse based on whether the orientation of the tool is within a predetermined threshold of the predetermined alignment orientation. For example, a lower light can be turned off when the handle of the tool is too low, thereby informing the user that the handle needs to be raised to reach the predetermined alignment orientation.

In an embodiment, one or more lights of the light source change color based on whether the orientation of the tool is within a predetermined threshold of the predetermined alignment orientation. A red, yellow, or green color may indicate that the tool is out of position, close to position, or within a position (or within a predetermined threshold of the position) that is designated (e.g., by the user). For example, a green light may be generated when the orientation is within the predetermined threshold, and a red light may be generated when the orientation is outside of the predetermined threshold. The red light may be directed downward and/or a green light may be directed upward when the handle of the tool is too low to provide the user with feedback regarding how the orientation of the tool should be to better match the predetermined alignment orientation.

In some embodiments, the light source is configured to adjust based on a predetermined fixed angle or position value. For example, one or more lights of the lights source may light up in a predetermined orientation, sequence, and/or pattern to indicate that the tool is being used at the predetermined alignment orientation or a predetermined orientation relative to a designated orientation.

For example, the processor may be configured to receive a user input of a desired orientation in the x, y, z planes, and the instrument lighting can turn on/off and change color intermittently based on the current orientation to provide feedback to the user about the orientation. Independent differential feedback in each plane that can account for degrees of misalignment from the predetermined orientation can indicate to the user how to adjust the instrument to reach the predetermined orientation.

In some embodiments, the orientation sensor and/or the surgical awl is configured to provide audio and/or tactile feedback to the user based on whether the orientation of the tool is within the predetermined threshold of the predetermined alignment orientation.

As mentioned above, features of any of the above aspects may be combined with one another. For example, the tool may include a detachable orientation sensor that is partially fixable relative to an instrument body, or the tool may include an integrated orientation sensor. The tool may provide feedback (e.g., a digital read-out and/or light feedback) based on the orientation sensed by the orientation sensor and the heading set by the user.

Referring now to FIGS. 22-26C, a second embodiment of the orientation sensor is shown. It is to be appreciated that the second embodiment can be similar to the first embodiment of the orientation sensor shown in FIGS. 1-4. Accordingly, the same reference numbers used above with reference to features of the first embodiment can be also used with a "prime" notation in reference to similar features of the second embodiment. It is also to be appreciated that, unless otherwise set forth below, the components (and features thereof) of the orientation sensor 30' of the second embodiment can be similar to those of the first embodiment.

Figure 22:
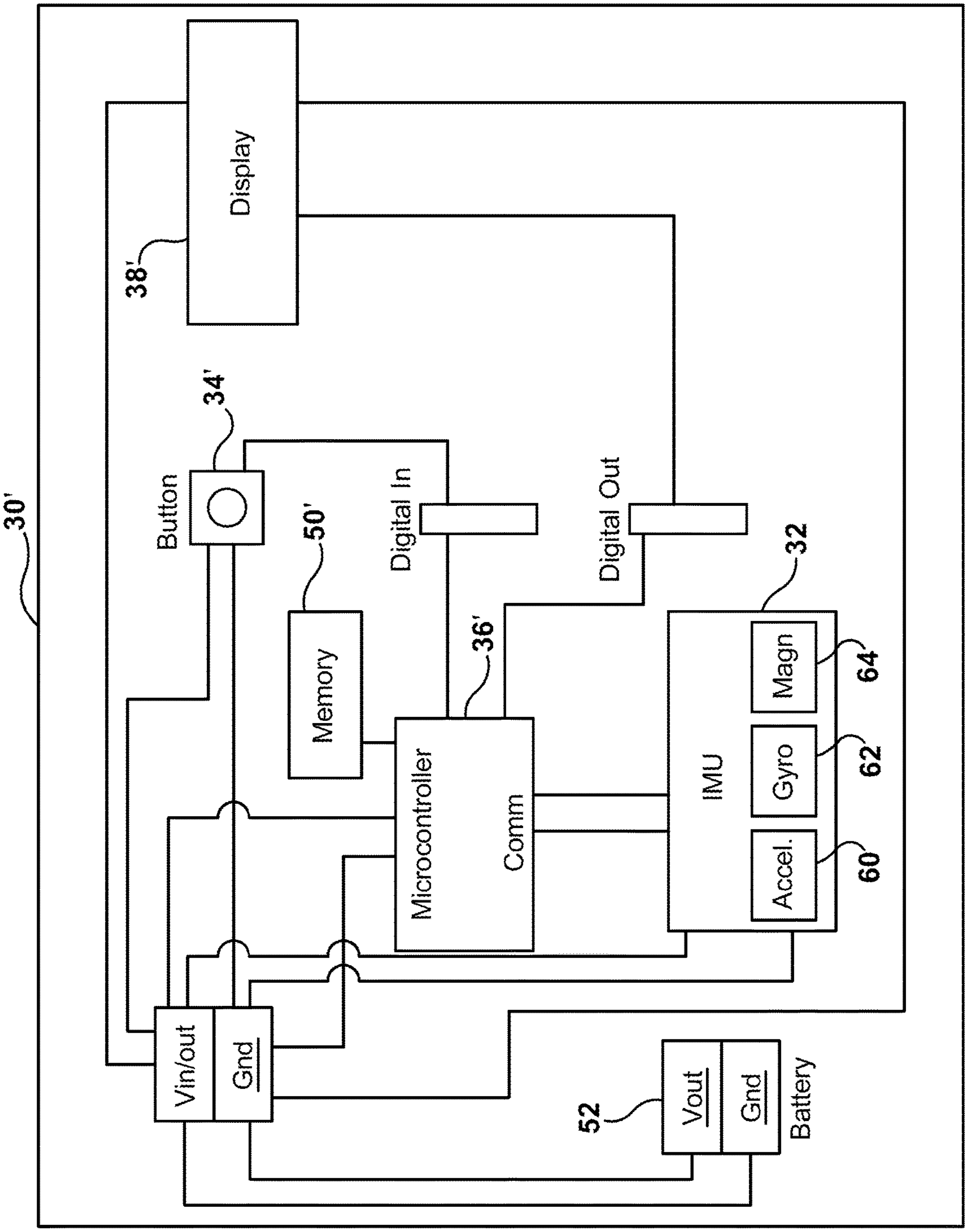
FIG. 22 is a block diagram of an orientation sensor of another embodiment that includes a user input device configured to change a mode of the orientation sensor.

FIG. 22 is a block diagram of an orientation sensor 30'. The orientation sensor 30' (e.g., an absolute orientation sensor) may include an orientation sensing component 32 (e.g., a 6-axis inertial measurement unit (IMU), or an absolute orientation sensing component, such as a 9-axis IMU), a user input device 34', a processor 36', and/or a display 38'. The orientation sensor 30' may include a memory 50', and/or a power source 52. The user input device 34', the processor 36', the display 38', and/or the memory 50' may be configured to perform each function discussed above with respect to the user input device 34, the processor 36, the display 37, and/or the memory 50 and further below.

For example, as with the display 38, the display 38' may be configured to display the prompt "pick axis," and the processor 36' may be configured to receive a predetermined user input from the user pressing the button 34' (an example of a user input device) when the prompt is displayed.

The orientation sensor 30' may have a first display mode and a second display mode. When the orientation sensor 30' is in the first display mode the display 38' may be configured to display at least one first orientation value, that is associated with the orientation data, in real-time. When the orientation sensor 30' is in the second mode the display 38' may be configured to display, in real-time, a respective at least one second orientation value that is associated with the plurality of orientation data and is different from the respective at least one second orientation value.

Figure 23B:
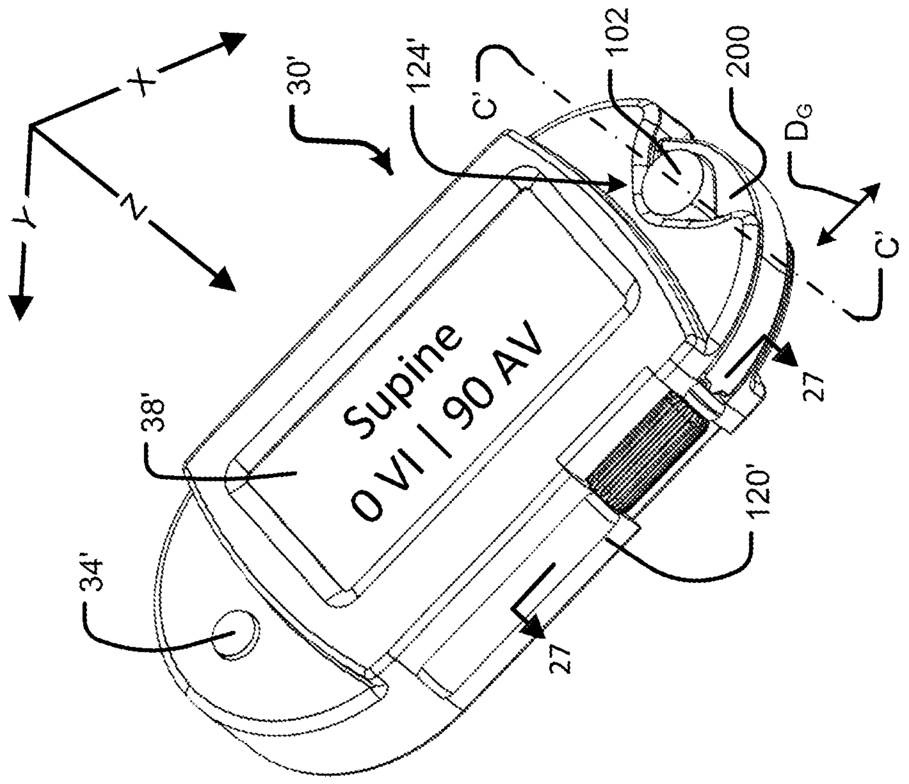
FIG. 23B is an oblique view of the orientation sensor of FIG. 23B when in a supine mode.
Figure 23A:
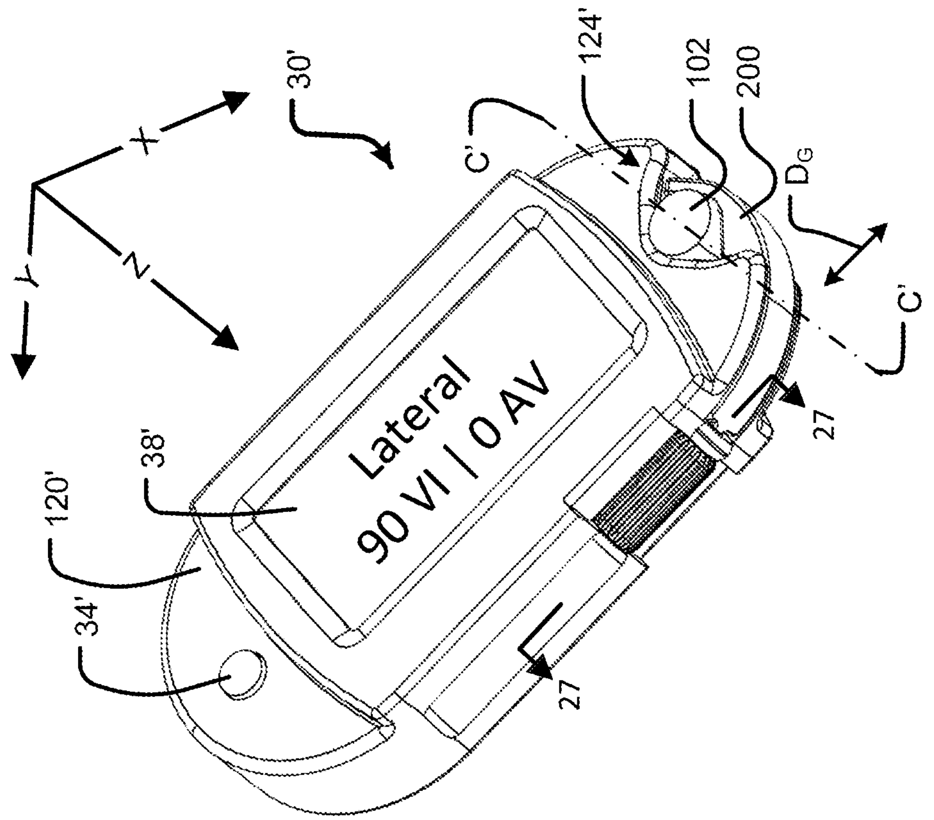
FIG. 23A is an oblique view of the orientation sensor of FIG. 22 when in a lateral mode.

For example, as exemplified in FIGS. 23A and 23B, the display 38' may be configured to display an indication of the current mode of the device. FIG. 23A illustrates an example of the orientation sensor 30' in the first mode (e.g., a lateral mode), in which the display 38' is configured to display "lateral," which may indicate that the displayed first orientation values correspond to an orientation relative to the surgery patient when the surgery patient is in a lateral position (e.g., on their side as exemplified in FIGS. 7-10, 15, and 16 above, on a surgical table, such that the patient faces in a direction along the horizontal plane). The first orientation values may be displayed as, for example, a vertical inclination ("VI") angle an anteversion ("AV") angle in degrees.

Figure 24A:
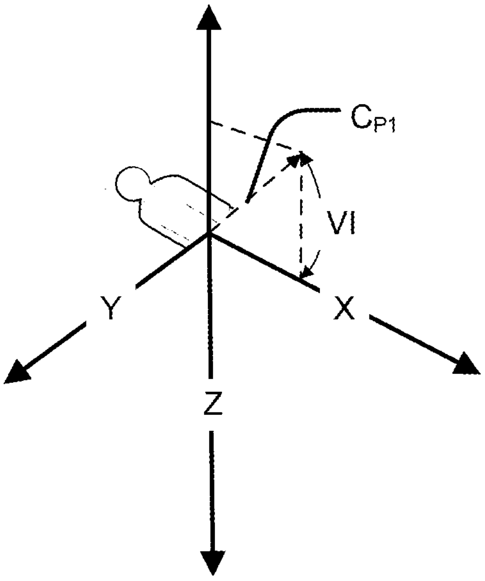
FIG. 24A is an oblique view of a patient in a lateral position and an example of a vertical inclination angle of the orientation sensor in the lateral mode.

With brief reference to FIG. 24A, the VI angle displayed in the lateral mode may correspond to the vertical inclination of the impactor shaft 102 relative to the X-Y plane (i.e., the horizontal plane as discussed above). FIG. 24A illustrates an example of a projection $C_{P1}$ of the guide axis C' and the impactor shaft 102 on the X-Z plane showing the VI angle.

Figure 24C:
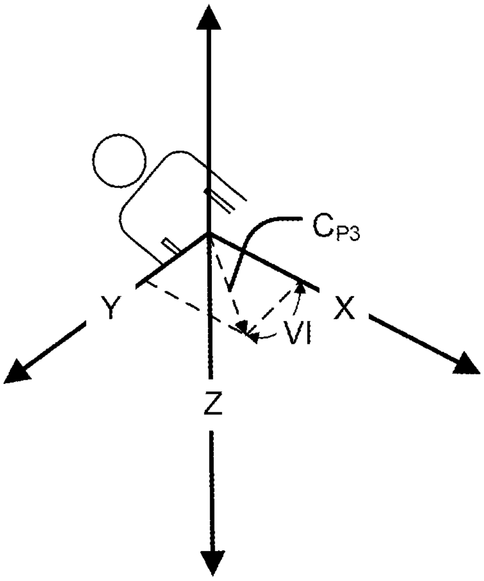
FIG. 24C is an oblique view of the patient in a supine position and an example of a vertical inclination angle of the orientation sensor in the supine mode.
Figure 24B:
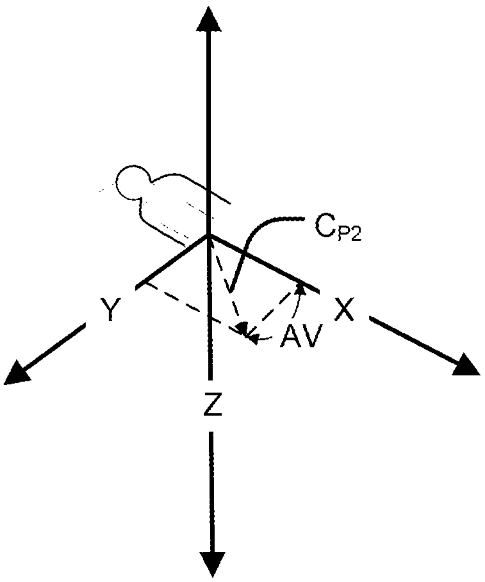
FIG. 24B is an oblique view of the patient in the lateral position and an example of an anteversion angle of the orientation sensor in the lateral mode.

With reference to FIG. 24B, the AV angle displayed in the lateral mode may correspond to the angle formed between the heading of the orientation sensor 30' (e.g., the X-axis—along the longitudinal body axis P—as discussed above) and the X-Z plane (e.g., a projection $C_{P2}$ of the current orientation of guide axis C' and the impactor shaft 102 on the horizontal plane X-Y. Thus, the AV angle may correspond to angular displacement within the horizontal plane. The heading of the orientation sensor 30' may be set as discussed above with respect to the orientation sensor 30.

The displayed values displayed in the lateral mode may remain the same (e.g., may not change in value) regardless of whether the orientation sensor 30' is rotated about the guide axis C' from a given position.

FIG. 23B illustrates an example of the orientation sensor 30' in the second mode (e.g., the supine mode), in which the display 38' is configured to display "supine," which may indicate that the displayed second orientation values are for when the surgery patient is in a supine position on the surgical table (e.g., on their back—rotated 90° about the longitudinal body axis P, such that the patient faces in a direction away from the horizontal plane vertically upward opposite the force of gravity). For example, the surgery patient may be rotated from the lateral position 90° about the longitudinal body axis P (shown in FIGS. 7-10, 15, and 16 above) and the X-axis so that the patient is face up on the surgical table.

The second orientation values may be displayed as, for example, a vertical inclination ("VI") angle an anteversion ("AV") angle in degrees. For example, when the orientation sensor is in a given position (e.g., attached to the impactor shaft 102—partially shown in FIGS. 23A and 23B—that is directly vertical, in line with Earth's gravity and the Z-axis), when in the first mode the display 38' may display a 90° vertical inclination angle and a 0° anteversion angle (see e.g., FIG. 23A), whereas when in the same position and in the second mode the display 38' may display a 0° vertical inclination angle and a 90° anteversion angle (see e.g., FIG. 23B).

The displayed values displayed in the supine mode may remain the same (e.g., may not change in value) regardless of whether the orientation sensor 30' is rotated about the guide axis C' from a given position.

With reference to FIG. 24C, the VI angle displayed in the supine mode may correspond to the angle formed between the heading of the orientation sensor 30' (e.g., the X-axis—along the longitudinal body axis P—as discussed above) and the X-Z plane (e.g., a projection $C_{P3}$ of the current orientation of guide axis C' and the impactor shaft 102 on the horizontal plane X-Y. Thus, the VI angle may correspond to angular displacement within the horizontal plane. The heading of the orientation sensor 30' may be set as discussed above.

Figure 24D:
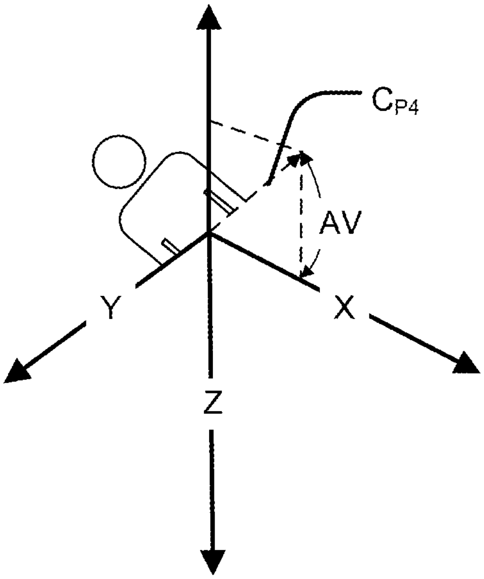
FIG. 24D is an oblique view of the patient in the supine position and an example of an anteversion angle of the orientation sensor in the supine mode.

With reference to FIG. 24D, the AV angle displayed in the supine mode may correspond to the vertical inclination of the impactor shaft 102 relative to the X-Y plane (i.e., the horizontal plane as discussed above). FIG. 24D illustrates an example of a projection $C_{P4}$ of the guide axis C' and the impactor shaft 102 on the X-Z plane showing the AV angle.

Turning back to FIGS. 23A and 23B, the button 34' may be configured to transition the display 38' from a first mode to a second mode, in response to the button 34' user input device receiving a first predetermined user input. In some embodiments, pressing the button may toggle between the first mode and the second mode (e.g., when the device is in an active state displaying real-time orientation values). In some embodiments, the orientation sensor has more than two modes and the button, in response to being pressed, is configured to transition the orientation sensor from each mode to another mode (e.g., in sequence from the first mode, to the second mode, to a third mode, etc. and after the last mode may loop back to the first mode). In some embodiments, a different user input device (e.g., a touch screen of the display) may be configured to receive user input to select the axis and/or to select the mode of the orientation sensor.

The orientation sensor may include a sensor body 120' that may define at least a portion of a guide 124' that is configured to mount to the impactor shaft 102 of an instrument body, wherein the guide 124' defines the guide axis C'.

As discussed above with reference to FIGS. 24A-24D, the first orientation values may include an angle of inclination of the guide axis C' relative to the X-Y plane and relative to an X-Z plane. When in the first mode, for example, the vertical inclination angle may be the amount of inclination of the guide axis C' relative to the X-Y plane (exemplified in FIG. 24A), and the anteversion angle may be the amount of inclination of the guide axis C' relative to the X-Z plane (exemplified in FIG. 24B). Thus, the display 38' may display the vertical inclination angle and the anteversion angle of the impactor shaft 102 during hip surgery of a patient in the lateral position, as represented schematically in FIGS. 24A and 24B.

Figure 25A:
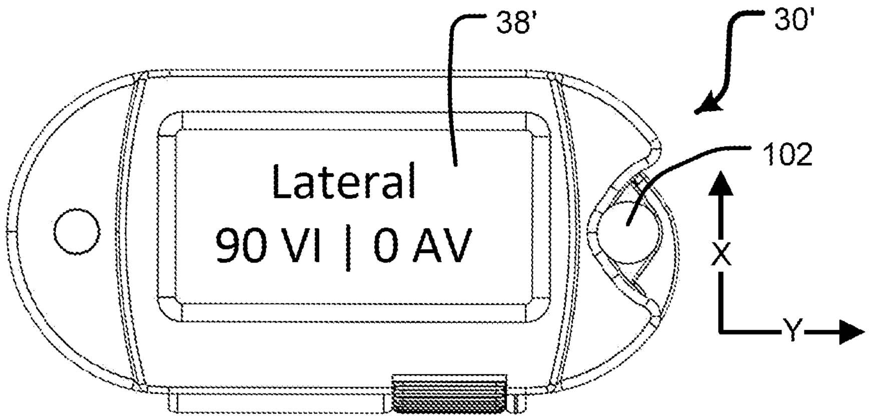
FIG. 25A is a front view of the orientation sensor of FIG. 23A when in the lateral mode and when a guide axis extends along a Z-axis.
Figure 25B:
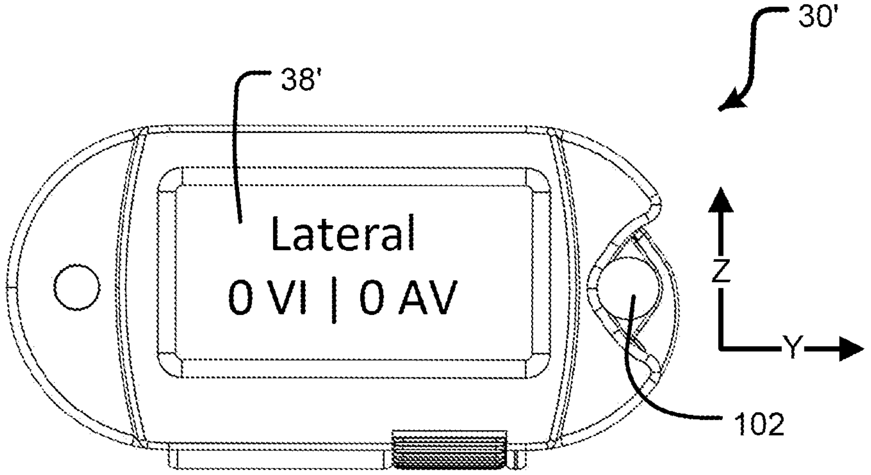
FIG. 25B is a front view of the orientation sensor of FIG. 23A when in the lateral mode and when the guide axis extends along an X-axis.
Figure 25C:
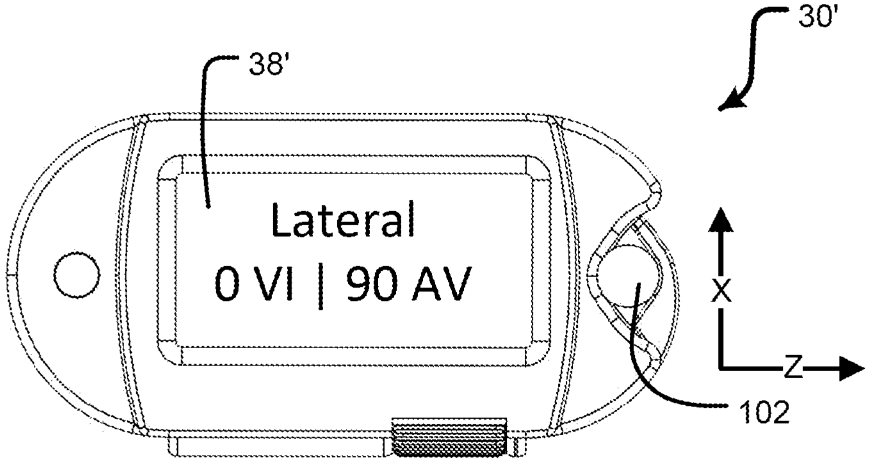
FIG. 25C is a front view of the orientation sensor of FIG. 23A when in the lateral mode and when the guide axis extends along a Y-axis.

FIGS. 25A-25C illustrate an example of the orientation sensor 30' attached to the impactor shaft 102 and at various orientations when in the lateral mode. FIG. 25A illustrates the impactor shaft 102 extending along the Z-axis where the display 38' may display a VI of 90° and an AV of 0°. FIG. 25B illustrates the impactor shaft 102 extending along the along the X-axis where the display 38' may display a VI of 0° and an AV of 0°. FIG. 25C illustrates the impactor shaft 102 extending along the Y-axis where the display 38' may display a VI of 0° and an AV of 90°.

When in the second mode, for example, vertical inclination angle of the second orientation values may be the amount of inclination of the guide axis C' relative to the X-Z plane (exemplified in FIG. 24C), and the anteversion angle of the second orientation values may be the amount of inclination of the guide axis C' relative to the X-Y plane (exemplified in FIG. 24D). Thus, the display 38' may display the vertical inclination angle and the anteversion angle of the impactor shaft during hip surgery of a patient in the supine position, as represented schematically in FIGS. 24C and 24D.

When the impactor shaft 102 is holding the acetabular cup 150 in a desired location of the pelvis, the heading has been set to the longitudinal body axis P of the patient, the patient is lying on their side, and the orientation sensor 30' is set to the lateral mode, the display 38' may display the vertical inclination and anteversion angles based on the orientation of the impactor shaft 102. For example, the impactor shaft 102 may have an appropriate orientation when the vertical inclination is displayed as 45° and the anteversion angle is displayed as 20°, as exemplified in FIG. 28.

Figure 26A:
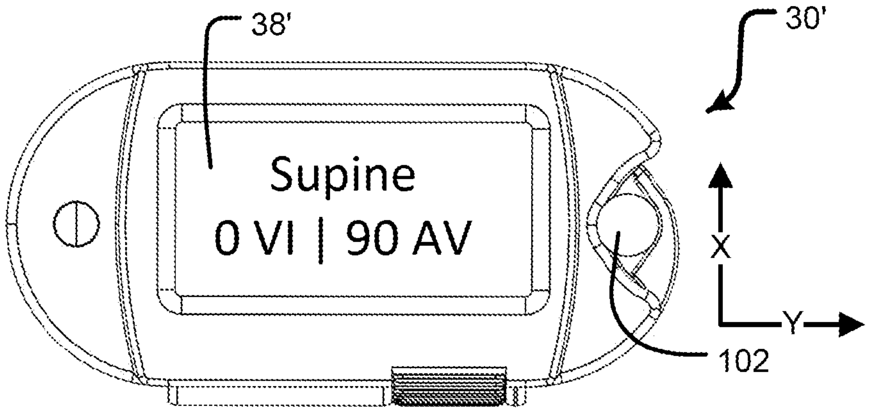
FIG. 26A is a front view of the orientation sensor of FIG. 23B when in the supine mode and when the guide axis extends along the Z-axis.
Figure 26B:
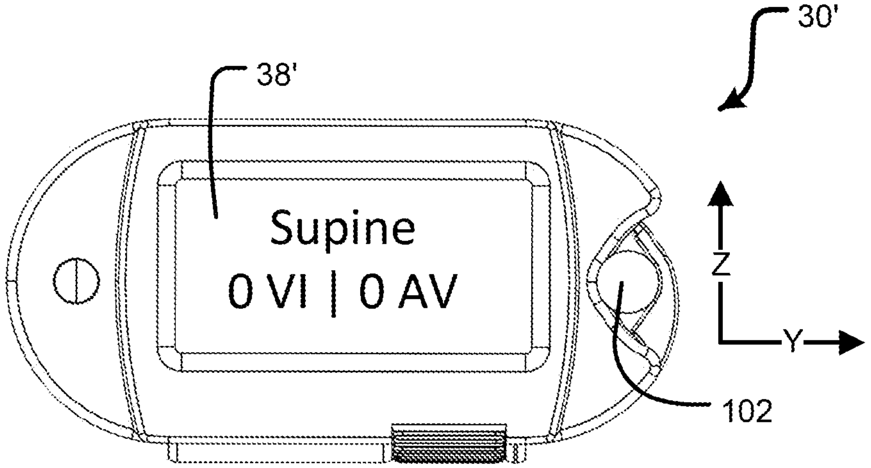
FIG. 26B is a front view of the orientation sensor of FIG. 23B when in the supine mode and when the guide axis extends along the X-axis.
Figure 26C:
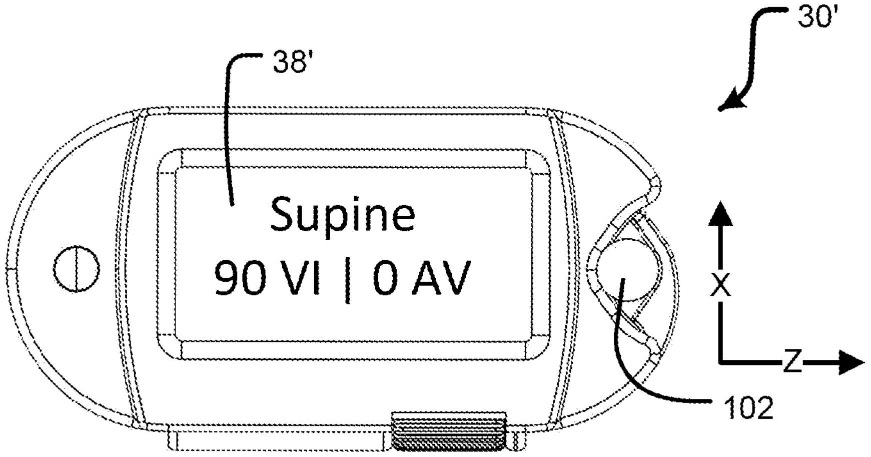
FIG. 26C is a front view of the orientation sensor of FIG. 23B when in the supine mode and when the guide axis extends along the Y-axis.

FIGS. 26A-26C illustrate an example of the orientation sensor 30' attached to the impactor shaft 102 and at various orientations when in the supine mode. FIG. 26A illustrates the impactor shaft 102 extending along the Z-axis where the display 38' may display a VI of 0° and an AV of 90°. FIG. 26B illustrates the impactor shaft 102 extending along the along the X-axis where the display 38' may display a VI of 0° and an AV of 0°. FIG. 26C illustrates the impactor shaft 102 extending along the Y-axis where the display 38' may display a VI of 90° and an AV of 0°.

When the impactor shaft 102 is holding the acetabular cup 150 in a desired location of the pelvis, the heading has been set to the longitudinal body axis P of the patient, the patient is lying on their back, and the orientation sensor 30' is set to the supine mode, the display 38' may display the vertical inclination and anteversion angles based on the orientation of the impactor shaft 102. For example, the impactor shaft 102 may have an appropriate orientation, different from the appropriate orientation of the impactor shaft 102 when the patient is lying on their side, when the vertical inclination is displayed as 45° and the anteversion angle is displayed as 20° in the supine mode.

In some embodiments, one or more of respective second orientation values may be different from one or more respective second orientation values by a predetermined amount. For example, when the orientation sensor 30' is in a given orientation and the first mode, the anteversion value may be different from the respective anteversion angle of the second mode by the predetermined amount (e.g., 90°) when the orientation sensor transitions to the second mode while in the given orientation.

Referring again to FIGS. 23A and 23B, the orientation sensor 30' may include a movable guide member 200 that at least partially defines the guide 124'. The movable guide member 200 may be movable along a guide member axis $D_G$ that is orthogonal to the guide axis C'. The movable guide member 200 may translationally extend from an initial position shown in FIGS. 23A and 23B to an extended position shown in FIG. 28.

When the movable guide member 200 is in the initial position, the movable guide member 200 may be configured to attach to the instrument body. For example, the guide 124' defined by the movable guide member 200 and the orientation sensor body 120' may fixedly attach to the impactor shaft 102 such that the guide axis C' remains fixed relative to the impactor shaft 102. In some embodiments, the orientation sensor 30' may not be rotatable relative to the impactor shaft 102, when attached. In some other embodiments, the orientation sensor 30' may be rotatable relative to the impactor only after application of an external force (e.g., a user urging the orientation sensor 30' to rotate about the impactor shaft).

When the movable guide member 200 translates along the guide member axis $D_G$ (e.g., to first and second extended positions exemplified in FIGS. 28 and 29, respectively) the guide 124' may be configured to receive the impactor shaft 102. For example, the orientation sensor body 120' and the movable guide member 200 may together define a lateral opening that opens in a direction orthogonal to the guide axis C' and the guide member axis $D_G$, when the movable guide member 200 is extended from the initial position.

Figure 28:
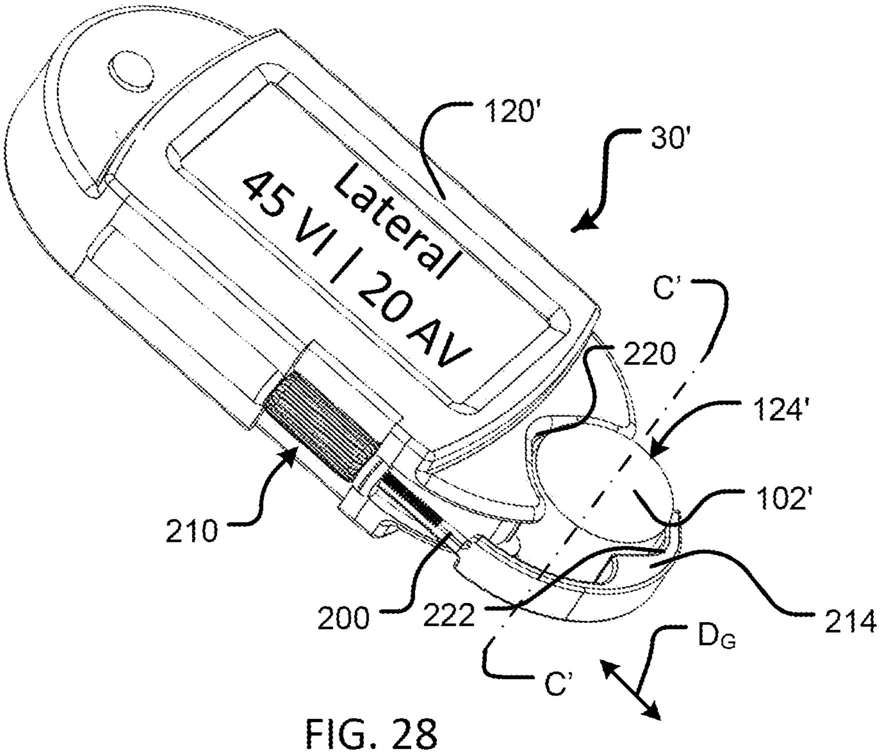
FIG. 28 is an oblique view of the orientation sensor of FIG. 23A in which the movable guide member is extended to attach to a larger impactor shaft, and the impactor shaft is at a desired vertical inclination and anteversion angle while the patient is lying on their side.
Figure 29:
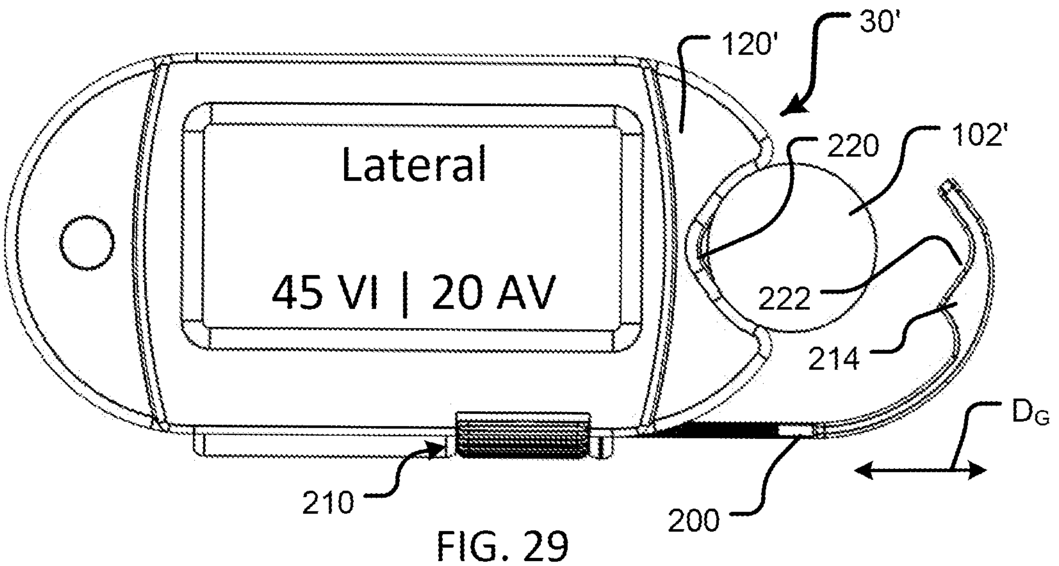
FIG. 29 is a front view of the orientation sensor of FIG. 28 in which the movable guide member is extended further to remove the larger impactor shaft.

The lateral opening may be widened by moving the movable guide member 200 from the first extended position shown in FIG. 28 to the second extended position shown in FIG. 29. For example, the movable guide member 200 may be extended to receive a larger instrument body (e.g., an impactor shaft 102' with a larger diameter, or anywhere from 5 millimeter (mm) to 30 mm, or anywhere from 10 mm to 22 mm) than the instrument body illustrated in part in FIG. 23A. When in the first extended position shown in FIG. 28, the guide 124' defined by the movable guide member 200 and the orientation sensor body 120' may fixedly attach to the larger impactor shaft 102' such that the guide axis C' remains fixed relative to the larger impactor shaft. In some embodiments, the orientation sensor 30' may not be rotatable relative to the larger impactor shaft, when attached.

The orientation sensor 30' may include an actuator 210 that is configured to actuate the movable guide member 200. For example, the actuator 210 may be configured to rotate about the guide member axis $D_G$ such that rotation in a first direction extends the movable guide member 200 and rotation in a second direction opposite to the first retracts the movable guide member 200. The actuator 210 may be translationally fixed relative to the orientation sensor body such that the actuator is unable to move except for rotate about the movable guide axis $D_G$ relative to the orientation sensor body.

Figure 27:
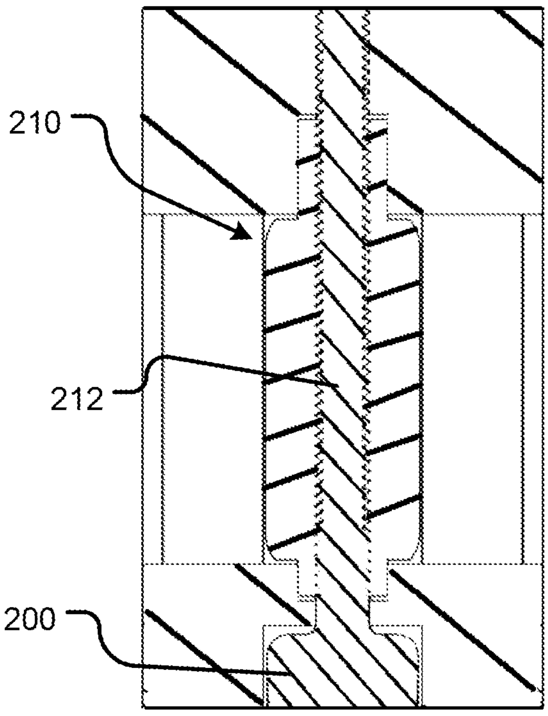
FIG. 27 is a partial cross-sectional view of the orientation sensor of FIGS. 23A and 23B including an actuator and a portion of a movable guide member.

Turning to FIG. 27, the actuator 210 may include a threaded inner portion that engages with corresponding external threads of a shaft 212 of the movable guide member 200 such that rotation of the actuator 210 about the guide member axis $D_G$ translates the movable guide member 200 along the guide member axis $D_G$.

Figure 30:
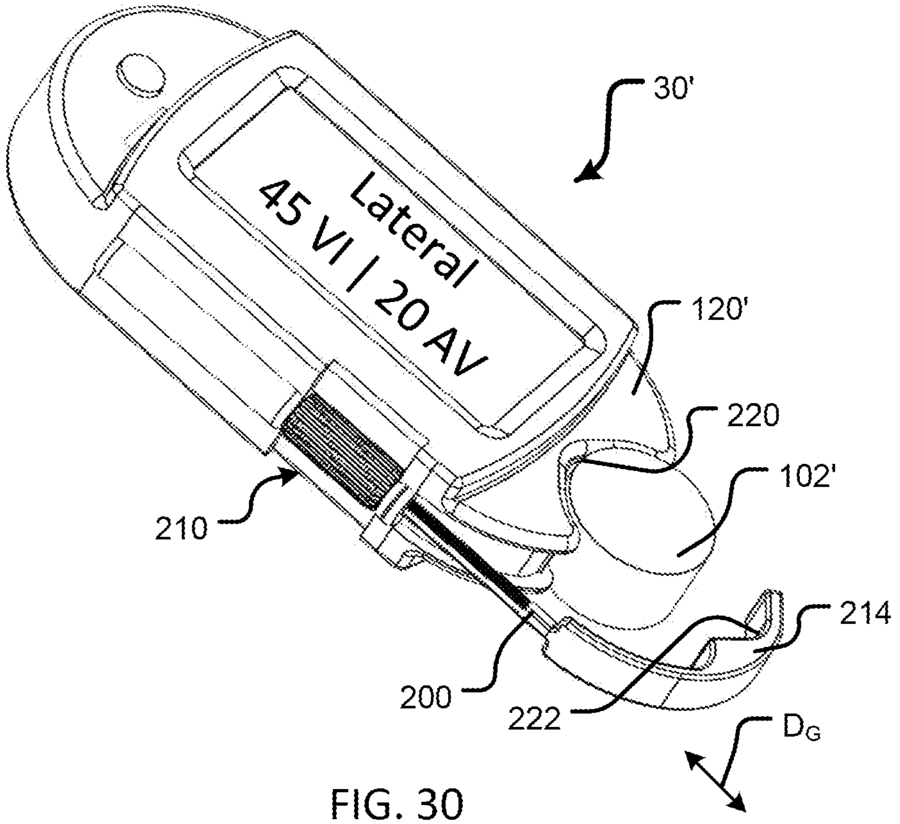
FIG. 30 is an oblique view of the orientation sensor of FIG. 29.

Referring now to FIGS. 28-30, the movable guide member 200 may include a movable jaw 214 that together with the orientation sensor body 120" defines the guide 124' (e.g., when attached to the impactor shaft 102' in FIG. 28). The movable jaw 214 and the orientation sensor body 120" may define respective V-shaped surfaces 220 and 222 that face one another and are configured to engage the impactor shafts 102 and 102'. The V-shaped surfaces 220 and 222 may provide for attaching to instrument bodies with different sizes and/or different shapes. In some embodiments, the movable jaw and/or the orientation sensor define respective surfaces of a different shape that face one another to engage the impactor shaft.

Figure 31:
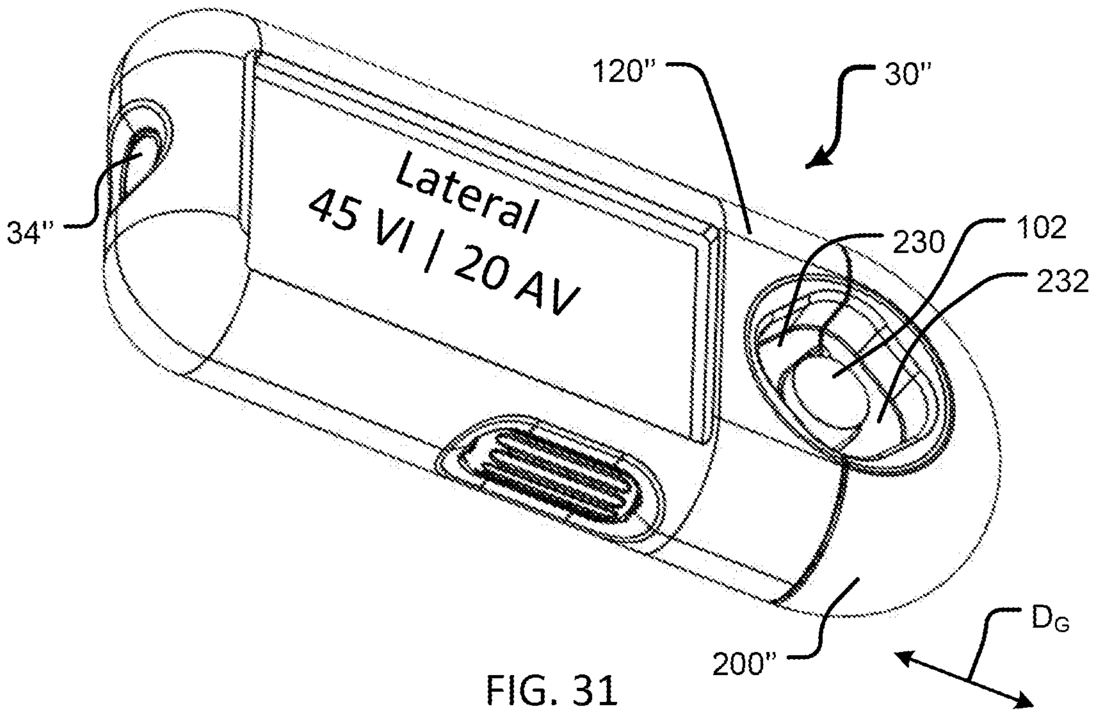
FIG. 31 is an oblique view of another embodiment of an orientation sensor in an initial position.
Figure 32:
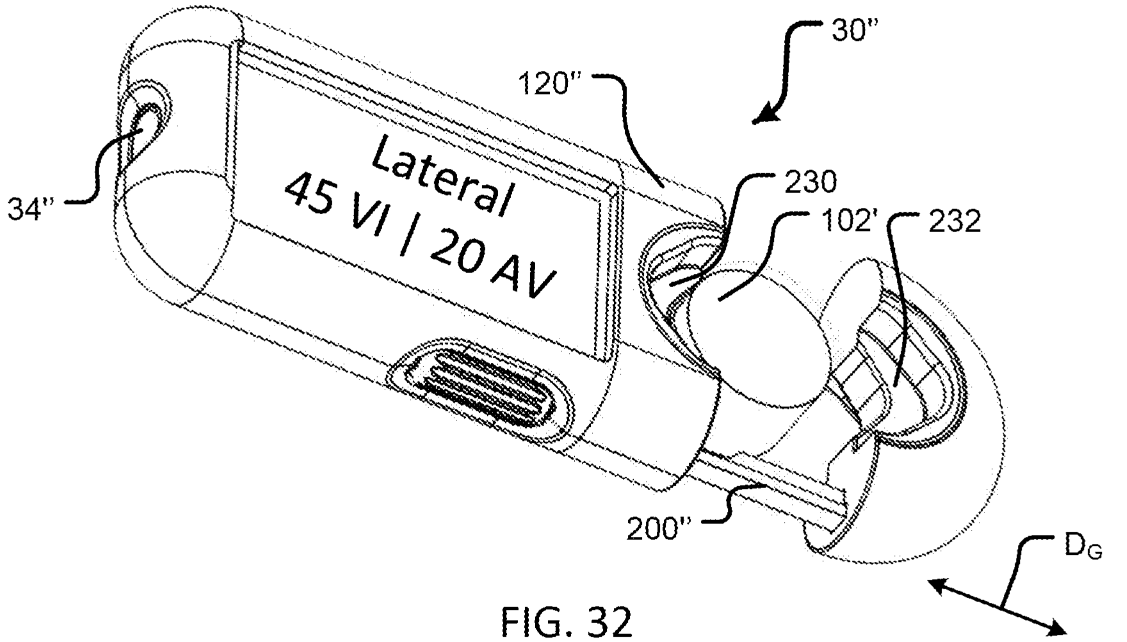
FIG. 32 is an oblique view of the orientation sensor of FIG. 31 in which a movable guide member is in an extended position.

Referring now to FIGS. 31 and 32, a third embodiment of the orientation sensor is shown. It is to be appreciated that the third embodiment can be similar to the second embodiment of the orientation sensor shown in FIGS. 23A and 23B. Accordingly, the same reference numbers used above with reference to features of the first or second embodiments can be also used with a “double prime” notation in reference to similar features of the third embodiment. It is also to be appreciated that, unless otherwise set forth below, the components (and features thereof) of the orientation sensor 30" of the third embodiment can be similar to those of the first and the second embodiments.

The orientation sensor 30" may include an orientation sensor body 120", a user input device 34", and a movable guide member 200". For example, the user input device 34" may be disposed at an end of the orientation sensor body 120" opposite the movable guide member 200" along a guide member axis $D_G$.

The movable guide member 200" may include a movable jaw" that together with the orientation sensor body 120" defines a guide 124". The movable jaw" and the sensor body 120" may include respective flanges 230 and 232 that define respective V-shaped surfaces that face one another and are configured to engage the impactor shafts 102 or 102'.

Figure 33:
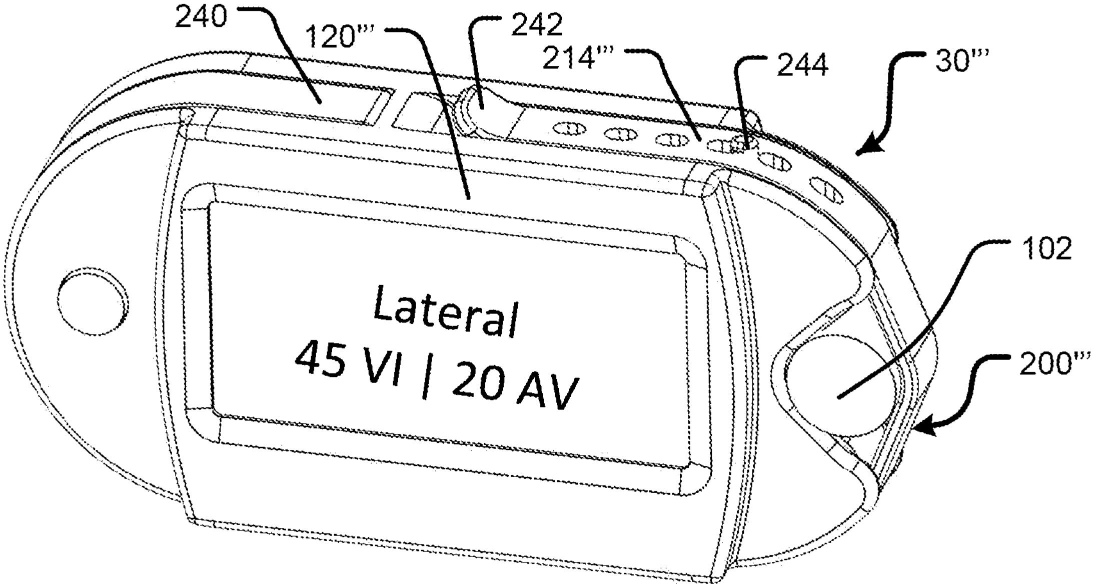
FIG. 33 is an oblique view of another embodiment of an orientation sensor including a belt in an initial position.
Figure 34:
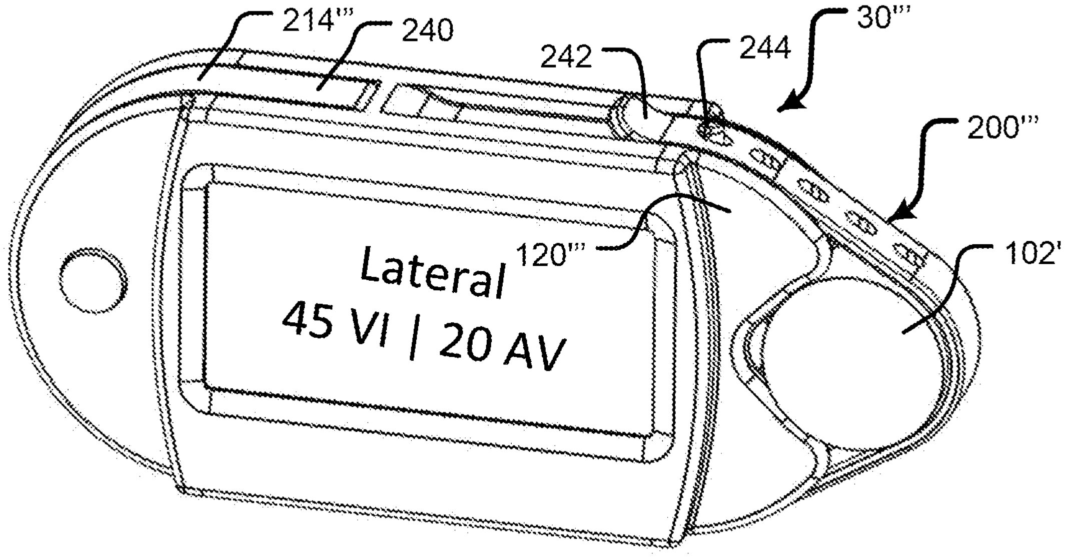
FIG. 34 is an oblique view of the orientation sensor of FIG. 33 in which the belt is in an extended position.

Referring now to FIGS. 33 and 34, a fourth embodiment of the orientation sensor is shown. It is to be appreciated that the fourth embodiment can be similar to the first, second, and third embodiments of the orientation sensor. Accordingly, the same reference numbers used above with reference to features of the first, second, and/or third embodiments can be also used with a “triple prime” notation in reference to similar features of the fourth embodiment. It is also to be appreciated that, unless otherwise set forth below, the components (and features thereof) of the orientation sensor 30'" of the fourth embodiment can be similar to those of the first, the second, and the third embodiments.

The orientation sensor 30'" may include an orientation sensor body 120'" and a movable guide member 200'". The movable guide member may include a belt 214'" that is configured to attach to the impactor shafts 102 or 102'. For example, the belt 214'" may include a fixed end 240 that is fixed relative to the orientation sensor body 120'" and a free end 242 that is movable relative to the orientation sensor body 120'". The free end 242 may be movable to a position where the belt 214''' wraps around a lateral side of the orientation sensor body 120''' and the impactor shaft 102 or 102'.

When the belt 214''' is wrapped around the orientation sensor body 120''' and the impactor shaft 102 or 102', the free end 240 may be attached to the orientation sensor body 120'''. For example, the orientation sensor body 120''' may include a protrusion 244 that is received in a respective hole of the belt to secure the impactor shaft 102 or 102' in a guide 124''' formed between the orientation sensor body 120''' and the belt 214'''.

Figure 35:
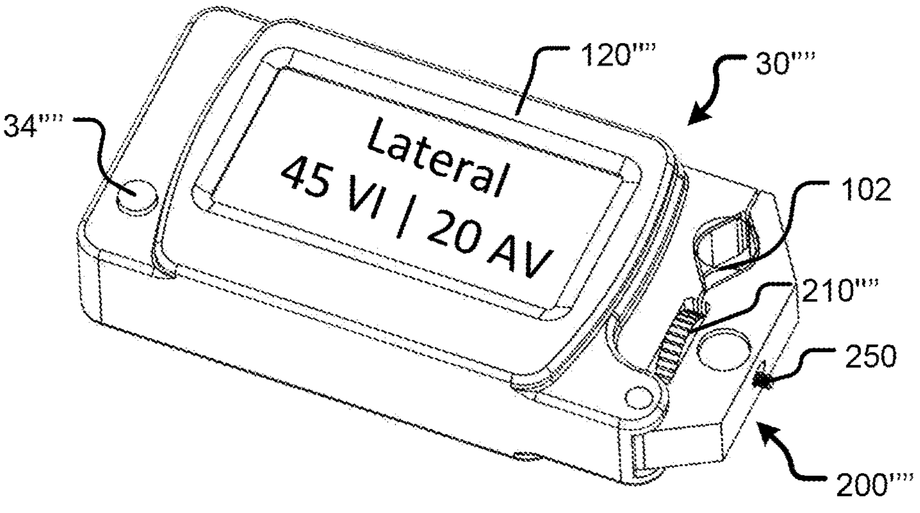
FIG. 35 is an oblique view of another embodiment of an orientation sensor including a movable guide member that is configured to rotate.
Figure 36:
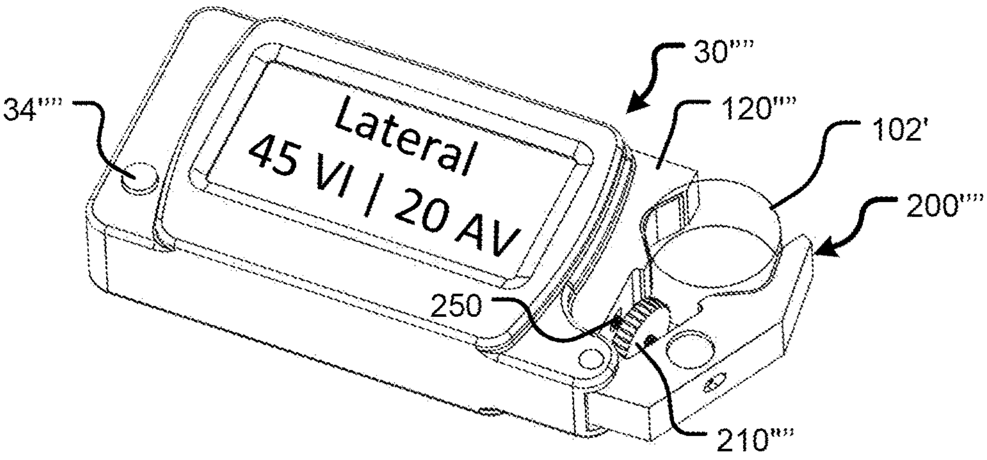
FIG. 36 is an oblique view of the orientation sensor of FIG. 35 in which the movable guide member is in an extended position.
Figure 37:
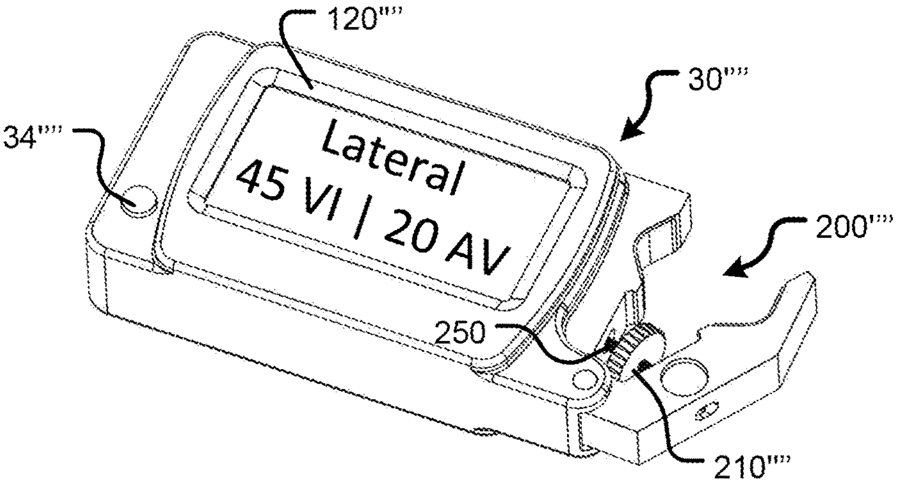
FIG. 37 is an oblique view of the orientation sensor of FIG. 35 in which the movable guide member is in a further extended position.

Referring now to FIGS. 35-37, a fifth embodiment of the orientation sensor is shown. It is to be appreciated that the fifth embodiment can be similar to the first, second, third, and fourth embodiments of the orientation sensor. Accordingly, the same reference numbers used above with reference to features of the first, second, third, and/or fourth embodiments can be also used with a "quadruple prime" notation in reference to similar features of the fifth embodiment. It is also to be appreciated that, unless otherwise set forth below, the components (and features thereof) of the orientation sensor 30'''' of the fifth embodiment can be similar to those of the first, second, third, and fourth embodiments.

The orientation sensor 30'''' may include an orientation sensor body 120'''', a user input device 34'''', a movable guide member 200'''', and an actuator 210''''. The movable guide member 200'''' may be rotatably coupled to the orientation sensor body 120'''' such that the movable guide member 200'''' is configured to open away from the position shown in FIG. 35 to the position shown in FIG. 37. For example, the actuator 210'''' may be fixed relative to a threaded shaft 250 that is configured to open the movable guide member 200'''' when the actuator 210'''' is rotated in a first direction about a rotational axis of the threaded shaft. The threaded shaft 250 may be configured to close the movable guide member 200'''' when the actuator 210'''' is rotated in a second direction opposite the first direction about a rotational axis of the threaded shaft 250.

For clarity, FIGS. 35 and 36 illustrate an example of a portion of the impactor shafts 102 and 102', respectively, transparently so that the orientation sensor 30'''' is more clearly visible when depicted as attached to one of the impactor shafts 102 or 102'.

Figure 38:
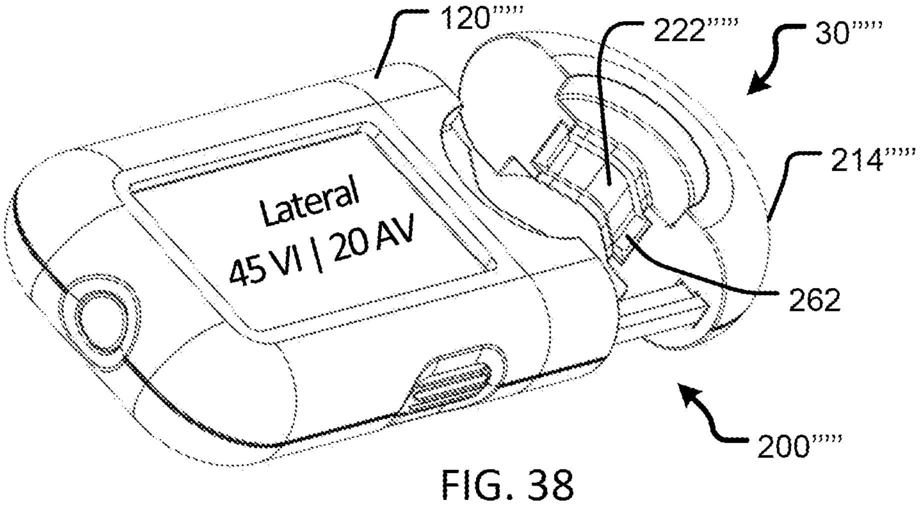
FIG. 38 is an oblique view of another embodiment of an orientation sensor including pads that are engageable with an impactor shaft.
Figure 39:
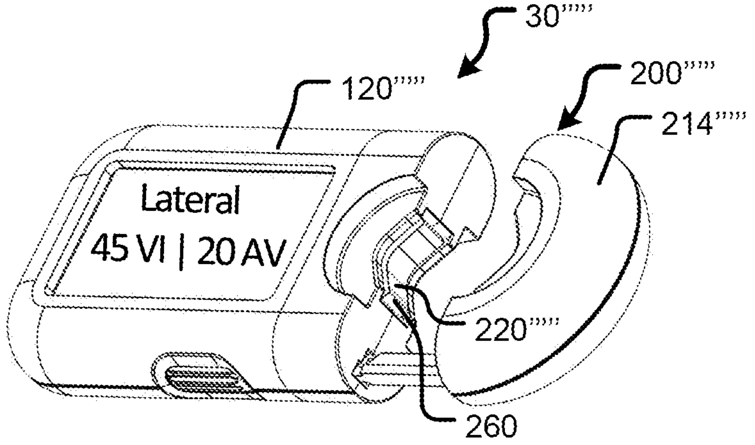
FIG. 39 is another oblique view of the orientation sensor of FIG. 38.
Figure 40:
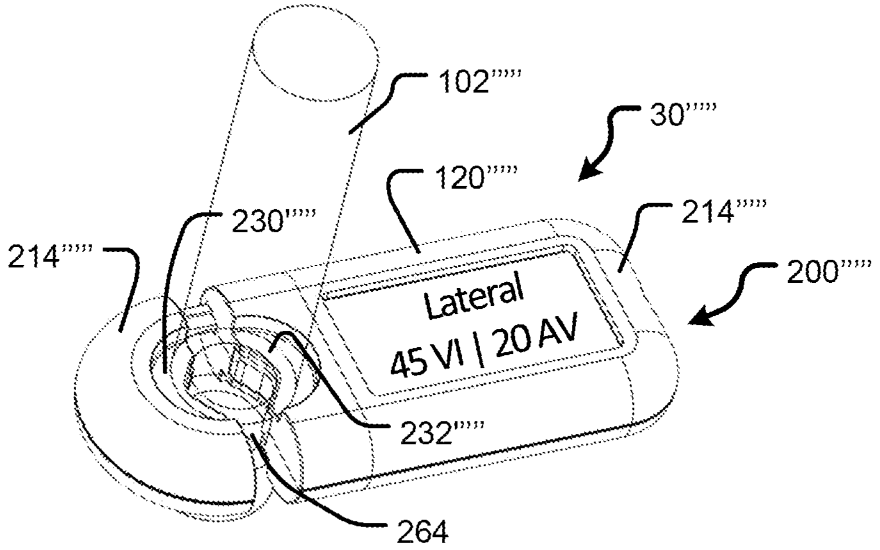
FIG. 40 is another oblique view of the orientation sensor of FIG. 38 in combination with an impactor shaft with a radially recessed portion.

Referring now to FIGS. 38-40, a sixth embodiment of the orientation sensor is shown. It is to be appreciated that the sixth embodiment can be similar to the first, second, third, fourth, and fifth embodiments of the orientation sensor. Accordingly, the same reference numbers used above with reference to features of the first, second, third, fourth, and/or fifth embodiments can be also used with a "quintuple prime" notation in reference to similar features of the sixth embodiment. It is also to be appreciated that, unless otherwise set forth below, the components (and features thereof) of the orientation sensor 30''''' of the sixth embodiment can be similar to those of the first, second, third, fourth, and fifth embodiments.

The orientation sensor 30''''' may include an orientation sensor body 120''''' and a movable guide member 200'''''. The movable guide member 200''''' may include a movable jaw 214''''' that together with the orientation sensor body 120''''' defines the guide 124'''''' (e.g., when attached to the impactor shaft 102'''''' in FIG. 40). The movable jaw 214''''' and the orientation sensor body 120''''' may each include a respective pad 260 or 262 that may define respective V-shaped surfaces 220''''' and 222''''' that face one another and are configured to engage the impactor shafts 102, 102', and 102'''''. The pads 260 and/or 262 may be configured to conform to the shape of the impactor shaft 102''''' and grip the impactor shaft 102'''''. For example, each pad 260 and/or 262 may be formed of a rubber material. In some embodiments, the pads are formed of another material that is softer than the material that forms the rest of the orientation sensor body and/or the movable jaw.

Referring now to FIG. 40, the impactor shaft 102''''' may include a radially recessed portion 264 (e.g., a circumferential groove) that is configured to receive the flanges 230''''' and 232'''''. For example, when the radially recessed portion 264 receives the flanges 230''''' and 232''''' the orientation sensor 30''''' may be axially fixed to the impactor shaft 120'''''. The flanges 230''''' and 232''''', for example, may engage axially facing surfaces that bound the radially recessed portion 264, thereby preventing axial movement of the orientation sensor 30''''' relative to the impactor shaft 120'''''.

For clarity, FIG. 40 illustrates an example of a portion of the impactor shaft 102''''' transparently so that the orientation sensor 30''''' is more clearly visible when depicted as attached to the impactor shaft 102'''''.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. An orientation sensor comprising:

an orientation sensing component that is configured to detect a plurality of orientation data, wherein the orientation sensor is configured to be mounted to an instrument body such that when the orientation sensor is mounted to the instrument body the orientation sensing component would be at least partially fixed relative to the instrument body such that a change in orientation of the instrument body in at least one direction would be detected by the orientation sensing component;

a display, wherein when the orientation sensor is in a first mode the display is configured to display at least one first orientation value, that is associated with the plurality of orientation data, in real-time, and when the orientation sensor is in a second mode the display is configured to display, in real-time, a respective at least one second orientation value that is associated with the plurality of orientation data and is different from the respective at least one first orientation value;

a user input device, wherein the user input device is configured to transition the display from the first mode to the second mode, in response to the user input device receiving a first predetermined user input; and a processor configured to, in response to the first predetermined user input, set a heading based on the orientation of the orientation sensor when the first predetermined user input is received, wherein the heading is a user-determined heading that is coplanar with a horizontal plane that is perpendicular to a direction of Earth's gravity, wherein when the orientation sensor is in the first mode the processor is configured to cause the display to display the at least one first orientation value, in real-time, and when the orientation sensor is in the second mode the processor is configured to cause the display to display, in real-time, the respective at least one second orientation value that is associated with the plurality of orientation data and is different from the respective at least one first orientation value.

2. The orientation sensor of claim 1, wherein the plurality of orientation data includes rotation data relative to an X-axis, a Y-axis, and a Z-axis, the Y-axis being perpendicular to the X-axis, and the Z-axis being perpendicular to the X-axis and the Y-axis;

wherein the orientation sensor includes a guide configured to mount to a shaft of the instrument body, wherein the guide defines a guide axis; and wherein the at least one first orientation value includes an angle of inclination of the guide axis relative to an X-Y plane and/or relative to an X-Z plane, and wherein the at least one second orientation value includes an angle of inclination of the guide axis relative to the X-Z plane and/or relative to the X-Y plane.

3. The orientation sensor of claim 2, wherein when in the first mode, the display is configured to display a first vertical inclination as an angle of the guide axis relative to the X-Y plane and is configured to display a first anteversion angle as an angle of the guide axis relative to the X-Z plane; and wherein when in the second mode, the display is configured to display a second vertical inclination as an angle of the guide axis relative to the X-Z plane and is configured to display a second anteversion angle as an angle of the guide axis relative to the X-Z plan.

4. The orientation sensor of claim 2, wherein the at least one first orientation value does not change when the orientation sensing component is rotated about the guide axis, and wherein the at least one second orientation value does not change when the orientation sensing component is rotated about the guide axis.

5. The orientation sensor of claim 1, wherein the respective at least one first orientation value is different from the respective at least one second orientation value by a predetermined amount, whereby when the orientation sensor is in a first orientation and the first mode the at least one first orientation value would be different from the respective at least one second orientation value by the predetermined amount when the orientation sensor transitions to the second mode while in the first orientation.

6. The orientation sensor of claim 1, wherein when in the first mode, the display is configured to display an indication that the display is in the first mode for a first position of a surgery patient, and wherein when in the second mode, the display is configured to display an indication that the display is in the second mode for a second position of a surgery patient, and wherein the first position of the surgery patient is one of a supine position and a lateral position, and wherein the second position of the surgery patient is the other of the supine position and the lateral position.

7. The orientation sensor of claim 1, wherein the user input device is configured to set the heading, in response to the user input device receiving a second predetermined user input, based on the orientation of the orientation sensor when the second predetermined user input is received by the user input device, wherein the at least one first orientation value and the at least one second orientation value are based on the heading set by the user input device.

8. The orientation sensor of claim 1, wherein the at least one first orientation value includes a first vertical inclination angle and a first anteversion angle, and the at least one second orientation value includes a second vertical inclination angle and a second anteversion angle.

9. The orientation sensor of claim 1, wherein the first mode is a lateral mode and the second mode is a supine mode.

10. The orientation sensor of claim 1, wherein the user input device is configured to transition the display from the second mode to the first mode, in response to the user input device receiving the first predetermined user input.

11. The orientation sensor of claim 1, wherein the processor is operably coupled to the display, the orientation sensing component, and the user input device, wherein the processor is configured to, in response to the user input device receiving a second predetermined user input, set the heading based on the orientation of the orientation sensor when the second predetermined user input is received by the user input device; and wherein the heading is associated with the orientation data such that when the orientation sensor would be in a predetermined reference orientation relative to the heading, the display displays a predetermined orientation value, and whereby movement of the orientation sensing component in the at least one direction from the predetermined reference orientation would be represented on the display as either 1) the at least one first orientation value being different from the predetermined orientation value when the orientation sensor is in the first mode, or 2) the at least one second orientation value being different from the predetermined orientation value when the orientation sensor is in the second mode.

12. The orientation sensor of claim 11, wherein the plurality of orientation data includes rotation data relative to an X-axis, a Y-axis, and a Z-axis, the Y-axis being perpendicular to the X-axis, and the Z-axis being perpendicular to the X-axis and the Y-axis; and wherein the heading is associated with the X-axis.

13. The orientation sensor of claim 1, wherein the orientation sensing component is an absolute orientation sensing component, and wherein the plurality of orientation data includes pitch data, roll data, and yaw data.

14. The orientation sensor of claim 1, wherein the user input device is a touch input device, and wherein the display is configured to be remote from a sensor body of the orientation sensor that houses the orientation sensing component.

15. A surgical instrument including:

an instrument body; and the orientation sensor of claim 1, wherein the orientation sensor is configured to mount to the instrument body, and wherein orientation sensing component is configured to be removable from the instrument body by hand.

16. The orientation sensor of claim 1, further comprising:
a memory, wherein the user input device is configured to store a heading in the memory, in response to the user input device receiving a second predetermined user input, based on the orientation of the orientation sensor when the second predetermined user input is received by the user input device, wherein the at least one first orientation value is based on the heading stored in the memory in response to the user input device receiving the second predetermined user input when the sensor is in the first mode, and wherein the at least one second orientation value is based on the heading stored in the memory in response to the user input device receiving the second predetermined user input when the sensor is in the second mode.

17. The orientation sensor of claim 16,
wherein the processor is operably coupled to the display, the orientation sensing component, the user input device, and the memory;
wherein, in response to the user input device receiving the second predetermined user input, the processor is configured to store, in the memory, the heading based on the orientation of the orientation sensor when the second predetermined user input is received by the user input device;
wherein the processor is configured to generate orientation information based on the heading, that is stored in the memory, and the current orientation of the orientation sensor; and
wherein the heading is associated with the orientation data such that when the orientation sensor would be held in a predetermined reference orientation relative to the heading, the processor generates predetermined orientation information, and whereby movement of the orientation sensing component in the at least one direction from the predetermined reference orientation would be represented by the processor generating a first orientation information that is different from the predetermined orientation information.

18. The orientation sensor of claim 1, wherein
the orientation sensing component is operably coupled to the processor,
wherein the display is operably coupled to the processor, and
wherein the orientation sensor further comprises a movable guide member that at least partially defines a guide when in a first position, wherein the movable guide member is configured to attach to the instrument body when in the first position, and wherein the movable guide member is configured to open to a second position where the guide is configured to receive the instrument body.

19. The orientation sensor of claim 18, wherein when the movable guide member is in the second position the movable guide member is laterally offset from the first position such that the guide defines a lateral opening to receive the instrument body.

20. The orientation sensor of claim 19, wherein when the movable guide member is in the first position the guide defines the lateral opening having a first size, and when the movable guide member is laterally offset from the first position such into the second position, the lateral opening has a second size that is larger than the first size.

21. The orientation sensor of claim 18, further including an actuator configured to actuate the movable guide member from the first position to the second position.

22. The orientation sensor of claim 18, further including an orientation sensor body, wherein the movable guide member and the orientation sensor body define the guide, and wherein the movable guide member includes a movable jaw that is configured to translate or rotate relative to the orientation sensor body.

23. The orientation sensor of claim 18, wherein the movable guide member and an orientation sensor body of the orientation sensor each define a respective V-shaped surface configured to engage the instrument body.

24. The orientation sensor of claim 18, wherein the movable guide member is configured to fixedly attach the orientation sensor to a shaft of the instrument body with a diameter anywhere from 5 mm to 30 mm.

25. The orientation sensor of claim 1,
wherein the plurality of orientation data includes rotation data relative to an X-axis, a Y-axis, and a Z-axis, the Y-axis being perpendicular to the X-axis, and the Z-axis being perpendicular to the X-axis and the Y-axis;
wherein the orientation sensor includes a guide configured to mount to a shaft of the instrument body, wherein the guide defines a guide axis; and
wherein the at least one first orientation value includes an angle of inclination of the guide axis relative to an X-Y plane and/or relative to an X-Z plane, and wherein the at least one first orientation value does not change in value when the orientation sensing component is rotated about the guide axis.

26. The orientation sensor of claim 25, wherein the display is rotatable.

27. An orientation sensor comprising:
an orientation sensing component, wherein the orientation sensing component is configured to detect a plurality of orientation data, wherein the orientation sensor is configured to be mounted to an instrument body such that when the orientation sensor is mounted to the instrument body the orientation sensing component would be at least partially fixed relative to the instrument body such that a change in orientation of the instrument body in at least one direction would be detected by the orientation sensing component;
a display, wherein the display is configured to display at least one orientation value, that is associated with the plurality of orientation data, in real-time; and
a user input device, wherein the user input device is configured to set a heading that is coplanar with a horizontal plane that is perpendicular to a direction of gravity, in response to the user input device receiving a predetermined user input, based on the orientation of the orientation sensing component when the predetermined user input is received by the user input device, wherein the at least one orientation value is based on the heading set by the user input device.

28. The orientation sensor of claim 27, wherein the heading is associated with the orientation data such that when the orientation sensor would be held in a predetermined reference orientation relative to the heading, the display displays a predetermined orientation value, and whereby movement of the orientation sensing component in the at least one direction from the predetermined reference orientation would be represented on the display as the at least one orientation value being different from the predetermined orientation value, wherein the heading is a user-determined heading that is coplanar with the horizontal plane regardless of the orientation of the orientation sensing component when the predetermined user input is received by the user input device, wherein the display is operably coupled to the orientation sensing component, and the user input device is operably coupled to the display, and the orientation sensor further includes a memory, and wherein the user input device is configured to store the heading in the memory, in response to the user input device receiving the predetermined user input, based on the orientation of the orientation sensor when the predetermined user input is received by the user input device, wherein the at least one orientation value is based on the heading stored in the memory; and wherein the orientation sensor includes a processor that is configured to, in response to the user input device receiving the predetermined user input, set the heading that is coplanar with the horizontal plane.

29. The orientation sensor of claim 27, wherein the heading is a user-determined heading that is coplanar with a horizontal plane relative to the Earth regardless of the orientation of the orientation of the orientation sensing component when the predetermined user input is received by the user input device.

30. The orientation sensor of claim 27, wherein the orientation sensor includes a transmitter, and the display is configured to be remote from a sensor body of the orientation sensor that houses the orientation sensing component.

31. The orientation sensor of claim 27, wherein the display and the orientation sensing component are housed in a sensor body of the orientation sensor.

32. An orientation sensor comprising:

an orientation sensing component, wherein the orientation sensing component is configured to detect a plurality of orientation data, wherein the orientation sensor is configured to be mounted to an instrument body such that when the orientation sensor is mounted to the instrument body the orientation sensing component would be at least partially fixed relative to the instrument body such that a change in orientation of the instrument body in at least one direction would be detected by the orientation sensing component;

a display, wherein the display is configured to display at least one orientation value, that is associated with the plurality of orientation data, in real-time; and a user input device, wherein the user input device is configured to set a heading, in response to the user input device receiving a predetermined user input, based on the orientation of the orientation sensor when the predetermined user input is received by the user input device, wherein the at least one orientation value is based on the heading set by the user input device;

wherein the orientation data includes rotation data relative to an X-axis, a Y-axis, and a Z-axis, the Y-axis being perpendicular to the X-axis, and the Z-axis being perpendicular to the X-axis and the Y-axis; and wherein the user input device is configured to set the heading, in response to the user input device receiving the predetermined user input, by only zeroing a rotation about the Z-axis, wherein the heading is entirely within a horizontal plane that is perpendicular to a direction of gravity and the Z-axis.

33. The orientation sensor of claim 32, wherein the heading is associated with the X-axis, wherein the X-axis and the Y-axis define a horizontal plane, and the Z-axis is vertical relative to the horizontal plane, and wherein the orientation data includes rotation data representation rotation of the orientation sensor about the Y-axis and the Z-axis; and wherein the orientation sensor includes a processor that is configured to, in response to the user input device receiving the predetermined user input, set the heading to be horizontal relative to the Earth and entirely within a plane that is parallel to i) the X-axis; and ii) a plane that is parallel to a longitudinal axis of the orientation sensor and the Z-axis.

34. The orientation sensor of claim 33, wherein the horizontal plane is defined relative to the Earth and the Z-axis is vertical relative to the Earth.

35. The orientation sensor of claim 32, wherein the display is configured to be remote from a sensor body of the orientation sensor that houses the orientation sensing component.

36. The orientation sensor of claim 32, further comprising a processor that is configured to, in response to the user input device receiving the predetermined user input, set the heading by only zeroing the rotation about the Z-axis.

37. The orientation sensor of claim 32, wherein the display and the orientation sensing component are housed in a sensor body of the orientation sensor.

* * * * *